United States Patent [19]

Schubert et al.

[11] Patent Number: 5,116,826
[45] Date of Patent: May 26, 1992

[54] SILAZANEOPHYL SULFIDES, AND THEIR USE AS PESTICIDES

[75] Inventors: Hans H. Schubert, Frankfurt am Main; Gerhard Salbeck; Hans-Peter Krause, both of Hofheim am Taunus; Werner Knauf, Eppstein/Taunus; Anna Waltersdorfer, Frankfurt am Main; Manfred Kern, Lörzweiler, all of Fed. Rep. of Germany

[73] Assignee: Hoechst Aktiengesellschaft, Frankfurt am Main, Fed. Rep. of Germany

[21] Appl. No.: 637,304

[22] Filed: Jan. 3, 1991

Related U.S. Application Data

[62] Division of Ser. No. 327,971, Mar. 23, 1989, Pat. No. 5,002,957.

[30] Foreign Application Priority Data

Mar. 26, 1988 [DE] Fed. Rep. of Germany ....... 3810379

[51] Int. Cl.$^5$ .................. C07D 213/32; C07F 7/10; A01N 43/40
[52] U.S. Cl. ......................................... 514/63; 546/14
[58] Field of Search ............................. 546/14; 514/63

[56] References Cited

PUBLICATIONS

Schubert et al., Chemical Abstracts, vol. 113, entry 24231d (1990).

Primary Examiner—John M. Ford
Attorney, Agent, or Firm—Curtis, Morris & Safford

[57] ABSTRACT

Azaneophyl and silazaneophyl sulfides, processes for their preparation, agents containing them, and their use as pesticides Compounds of the formula I, their optical isomers and mixtures thereof $$R^1-\underset{\underset{R^3}{|}}{\overset{\overset{R^2}{|}}{M}}-CH_2-S-\underset{\underset{R^4}{|}}{CH}-R^5, \quad (I)$$

where
  M denotes C or Si,
  $R^1$ denotes unsubstituted or substituted pyridyl, unsubstituted or substituted pyrimidyl, and
    when M=C— denotes unsubstituted or substituted pyridazinyl, unsubstituted or substituted pyrazinyl, unsubstituted or substituted 1,2,4-triazinyl, unsubstituted or substituted 1,2,4,5-tetrazinyl,
  $R^2$, $R^3$ independently of one another denote alkyl, alkenyl, haloalkyl, phenyl, or $R^2$ and $R^3$ denote an alkylene chain which—together with the quaternary central atom (M)—form an unsubstituted or fluorine-substituted ring having four to six ring members (when M=Si) or having three to six ring members (when M=C),
  $R^4$ denotes H, F, —CN, —CCl$_3$, —C≡CH, (C$_1$-C$_4$)alkyl, $$-\underset{\underset{S}{\|}}{C}-NH_2,$$

$R^5$ denotes pyridyl, furyl, thienyl, all of which can be substituted, phthalimidyl, dialkylmaleinimidyl, thiophthalimidyl, dihydrophthalimidyl, tetrahydrophthalimidyl, substituted phenyl
  or $R^4$ and $R^5$—together with the carbon atom bridging them—denote an optionally substituted indanyl, cyclopentenoyl or cyclopentenyl radical, and to their salts and quaternization products for advantageous insecticidal, acaricidal or nematocidal properties.

5 Claims, No Drawings

SILAZANEOPHYL SULFIDES, AND THEIR USE AS PESTICIDES

This application is a division of application Ser. No. 07/327,971, filed Mar. 23, 1989, now U.S. Pat. No. 5,002,957.

DESCRIPTION

EP-A 0,249,015 describes the insecticidal and acaricidal action of certain silazaneophyl ethers and their hydrocarbon analogs. Furthermore, sulfur-containing silane derivatives are disclosed in EP-A 0,224,024, which also exhibit insecticidal and acaricidal activities.

Novel azaneophyl and silazaneophyl sulfides exhibiting advantageous insecticidal, acaricidal or nematocidal properties have now been found.

The present invention thus relates to the compounds of the formula (I), their optical isomers and possible mixtures thereof

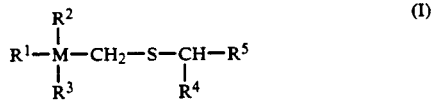

where

M denotes C or Si, $R^1$ denotes unsubstituted or substituted pyridyl, unsubstituted or substituted pyrimidyl, and—when M=C—denotes unsubstituted or substituted pyridazinyl, unsubstituted or substituted pyrazinyl, unsubstituted or substituted 1,2,4-triazinyl, unsubstituted or substituted 1,2,4,5-tetrazinyl, $R^2$, $R^3$ independently of one another denote ($C_1$-$C_3$)alkyl, ($C_2$-$C_8$)alkenyl, ($C_1$-$C_2$)haloalkyl, phenyl, or $R^2$ and $R^3$ denote an alkylene chain which—together with the quaternary central atom (M)—form an unsubstituted or fluorine-substituted ring having four to six ring members (when M=Si) or having three to six ring members (when M=C), $R^4$ denotes H, F, —CN, —CCl$_3$, —C≡CH, ($C_1$-$C_4$)alkyl,

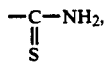

$R^5$ denotes pyridyl, furyl, thienyl, all of which can be substituted, phthalimidyl, di($C_1$-$C_4$)alkylmaleinimidyl, thiophthalimidyl, dihydrophthalimidyl, tetrahydrophthalimidyl, substituted phenyl or $R^4$ and $R^5$—together with the carbon atom bridging them—denote an optionally substituted indanyl, cyclopentenoyl or cyclopentenyl radical, and to their salts and quaternization products which can be employed for agricultural purposes. In this case, the salt formation or quaternization is carried out by customary methods by an addition reaction of suitable compounds with the basic nitrogen atom or the basic nitrogen atoms of the heterocyclic radicals $R^1$ and/or $R^5$. Multiple salt formation or quaternization is thus possible.

Suitable acids for salt formation on the nitrogen are all inorganic or organic acids which, by virtue of their pKs value, are capable of salt formation, for example hydrohalic acids, nitric acid, sulfuric acid, phosphoric acid, phosphonic acid, sulfonic acid, haloacetic acids or oxalic acid.

A preferred optionally substituted pyridyl $R^1$, pyrimidyl $R^1$, pyridazinyl $R^1$, pyrazinyl $R^1$, 1,2,4-triazinyl $R^1$ or 1,2,4,5-tetrazinyl $R^1$ denotes a radical of the general formulae (A), (B), (C), (D), (E) or (F),

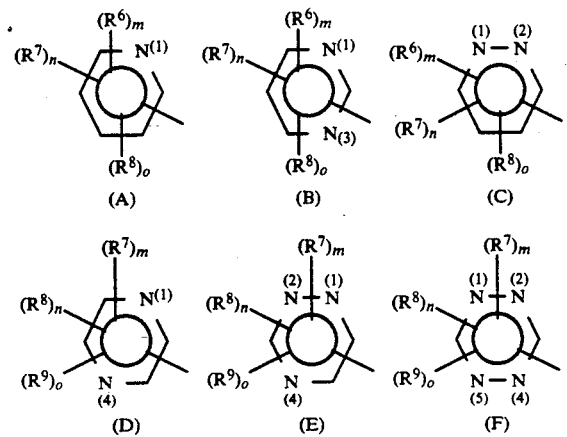

where $0 \leq m+n+o \leq 3$ and m, n, o may have the values 0 to 2. $R^6$, $R^7$, $R^8$ and $R^9$ independently of one another stand for ($C_1$-$C_5$)alkyl, halogen, ($C_2$-$C_6$)alkenyl, ($C_2$-$C_6$)alkynyl, ($C_3$-$C_7$)cycloalkyl, ($C_1$-$C_3$)alkoxy, ($C_2$-$C_4$)alkenyloxy, ($C_2$-$C_4$)alkynyloxy, ($C_1$-$C_4$)alkylthio, ($C_3$-$C_6$)cycloalkyloxy, ($C_1$-$C_4$)haloalkyl, ($C_1$-$C_3$)haloalkoxy, ($C_1$-$C_3$)haloalkylthio, ($C_2$-$C_5$)haloalkenyl, ($C_2$-$C_5$)haloalkenyloxy, ($C_2$-$C_5$)haloalkenylthio, or two of the radicals $R^6$, $R^7$, $R^8$, $R^9$—when they are in the ortho position—form a methylenedioxy, ethylenedioxy or ($C_3$-$C_5$)alkylene radical.

The linkage point (free valency) of the pyridyl radical (for example in formula (A)) on the quaternary central atom M in formula (I) is preferably in the 2- or 3-position of the pyridyl radical (N=position 1), particularly preferably in the 3-position of the pyridyl radical. The pyrimidyl radical (for example formula (B)) is preferably bonded to the quaternary central atom M in position 2 or 5. The preferred linkage point of the pyridazinyl radical (for example formula (C)) is position 3, that of the pyrazinyl radical (for example formula (D)) position 2. Triazinyl radicals (for example formula (E)) and tetrazinyl radicals (for example formula (F)) are preferably linked to the quaternary central atom in the 3- or 6-position, respectively. $R^1$ particularly preferably denotes mono- or disubstituted pyridyl, pryimidyl, pyridazinyl or pyrazinyl radicals of the formulae (A), (B), (C) or (D) where m+n+o=1 or 2, the substituents ($R^6$-$R^9$) being orientated in particular in the para or meta position to the linkage point (quaternary central atom M). $R^1$=A is of particular importance.

$R^2$ and $R^3$ preferably represent a ($C_1$-$C_3$)alkyl radical such as methyl, ethyl, i-propyl and n-propyl, a fluorinated methyl radical such as fluoromethyl, difluoromethyl and trifluoromethyl, or—when M=C—together with the carbon atom linking them preferably denote an unsubstituted or mono- or difluorinated cyclopropyl ring.

$R^4$ preferably represents hydrogen, fluorine, cyano or ($C_1$-$C_4$)alkyl, particularly preferably hydrogen.

Substituted phenyl $R^5$ preferably represents a phenyl radical of the general formula (G)

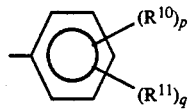

where $R^{10}$ and $R^{11}$—independently of one another—can denote halogen, $(C_1-C_4)$alkyl, $(C_1-C_4)$alkoxy, $(C_1-C_4)$haloalkyl, phenyl, N-pyrrolyl or a group of the general formula (H)

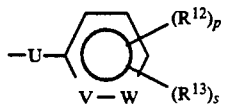

where $R^{12}$ and $R^{13}$ independently of one another denote H, halogen, $(C_1-C_4)$alkyl, $(C_1-C_4)$alkoxy and $(C_1-C_4)$haloalkyl; U denotes —$CH_2$—, C=O, —O— or —S—, preferably —O—; V, W denote CH or N, it being possible that both simultaneously denote CH but not N, and where in formulae (G) and (H)

p, q = an integer of 0 to 5 with the condition that the total p+q must denote a number from 1 to 5, r, s = 0, 1 or 2, with the condition that the total of r+s must be 0, 1 or 2, and the condition that, in the event that $R^{10}$ or $R^{11}$ corresponds to the group (H), p, q must denote 0 or 1, and p+q must denote 1 or 2.

Of these $R^5$ radicals, radicals of the formula (G), where $(R^{10})_p$ is H or 4-fluoro and $(R^{11})_q$ is orientated in the 3-position of the phenyl radical and denotes the radical

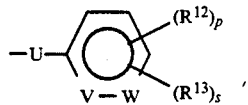

where r+s preferably stands for 0, are particularly important.

As an optionally substituted pyridyl, $R^5$ represents a mono- or disubstituted pyridyl group of the general formula (K)

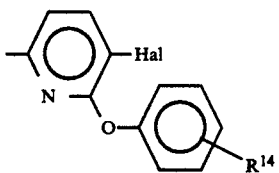

where $R^{14}$ denotes halogen with the exception of I, $(C_1-C_4)$alkyl, $(C_1-C_4)$alkoxy or $(C_1-C_4)$haloalkyl and Hal denotes halogen, in particular fluorine or H.

As an optionally substituted thienyl or furyl, $R^5$ represents a heterocycle of the general formula (L)

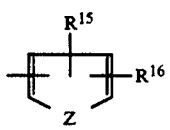

where
Z denotes O, S, $R^{15}$ denotes H, halogen, $(C_1-C_4)$alkyl, $(C_1-C_4)$alkoxy, $(C_1-C_4)$haloalkyl, CN or $NO_2$ and $R^{16}$ denotes a generally substituted benzyl, propargyl, allyl or phenoxy.

Substituted phenyl radicals as $R^5$ are of particular importance for the invention.

Typical examples which are indicated for the group $R^5$ are the following radicals:

Pentafluorophenyl, 5-benzyl-3-furyl, 4-phenoxyphenyl, 3-phenoxyphenyl, 3-(4-fluorophenoxy)phenyl, 3-(4-chlorophenoxy)phenyl, 3-(4-bromophenoxy)phenyl, 3-(3-fluorophenoxy)phenyl, 3-(3-chlorophenoxy)phenyl, 3-(3-bromophenoxy)phenyl, 3-(2-fluorophenoxy)phenyl, 3-(2-chlorophenoxy)phenyl, 3-(2-bromophenoxy)phenyl, 3-(4-methylphenoxy)phenyl, 3-(3-methylphenoxy)phenyl, 3-(2-methylphenoxy)phenyl, 3-(4-methoxyphenoxy)phenyl, 3-(3-methoxyphenoxy)phenyl, 3-(2-methoxyphenoxy)phenyl, 3-(4-ethoxyphenoxy)phenyl, 3-(phenylthio)phenyl, 3-(4-fluorophenylthio)phenyl, 3-(3-fluorophenylthio)phenyl, 3-benzoylphenyl, 3-benzylphenyl, 3-(4-fluorobenzyl)phenyl, 3-(4-chlorobenzyl)phenyl, 3-(3,5-dichlorophenoxy)phenyl, 3-(3,4-dichlorophenoxy)phenyl, 3-(4-chloro-2-methylphenoxy))phenyl, 3-(2-chloro-5-methylphenoxy)phenyl, 3-(4-chloro-5-methylphenoxy)phenyl, 3-(4-ethylenephenoxy)phenyl, 3-(3-chloro-5-methoxyphenoxy)phenyl, 3-(2,5-dichlorophenoxy)phenyl, 3-(3,5-dichlorobenzoyl)phenyl, 3-(3,4-dichlorobenzoyl)phenyl, 3-(4-methylbenzyl)phenyl, 3-(4-isopropoxyphenoxy)phenyl, 4-fluoro-3-phenoxyphenyl, 4-chloro-3-phenoxyphenyl, 4-bromo-3-phenoxyphenyl, 4-fluoro-3-(4-fluorophenoxy)phenyl, 4-fluoro-3-(4-chlorophenoxy)phenyl, 4-fluoro-3-(4-bromophenoxy)phenyl, 4-fluoro-3-(4-methylphenoxy)phenyl, 4-fluoro-3-(4-methoxyphenoxy)phenyl, 4-fluoro-3-(3-fluorophenoxy)phenyl, 4-fluoro-3-(3-chlorophenoxy)phenyl, 4-fluoro-3-(3-bromophenoxy)phenyl, 4-fluoro-3-(3-methoxyphenoxy)phenyl, 4-fluoro-3-(4-ethoxyphenoxy)phenyl, 4-fluoro-3-(2-fluorophenoxy)phenyl, 3-methoxy-5-phenoxyphenyl, 2-fluoro-3-phenoxyphenyl, 2-fluoro-3-(4-fluorophenoxy)phenyl, 2-fluoro-3-(3-fluorophenoxy)phenyl, 2-fluoro-3-(2-fluorophenoxy)phenyl, 3-fluoro-5-(4-fluorophenoxy)phenyl, 3-fluoro-5-(3-fluorophenoxy)phenyl, 3-fluoro-5-(2-fluorophenoxy)phenyl, 4-methyl-3-phenoxyphenyl, 3-fluoro-5-(4-methylphenoxy)phenyl, 3-fluoro-5-(3methoxyphenoxy)phenyl, 2-fluoro-5-(4-fluorophenoxy)phenyl, 2-fluoro-5-(3-fluorophenoxy)phenyl, 2-fluoro-5-(2-fluorophenoxy)phenyl, 2-chloro-3-phenoxyphenyl, 3-fluoro-5-phenoxyphenyl, 2-fluoro-5-phenoxyphenyl, 2-chloro-5-phenoxyphenyl, 2-bromo-5-phenoxyphenyl, 4-chloro-3-(3-methylphenoxy)phenyl, 4-chloro-3-(4-fluorophenoxy)phenyl, 3-chloro-5-phenoxyphenyl, 3-bromo-5-phenoxyphenyl, 4-bromo-3-phenoxyphenyl, 4-trifluoromethyl-3-phenoxyphenyl, 4-fluoro-3-phenylthiophenyl, 4-fluoro-3-benzylphenyl, 3-(2-pyridyloxy)phenyl, 3-(3-pyridyloxy)phenyl, 4-fluoro-3-(2-pyridyloxy)phenyl, 4-chloro-3-(2-pyridyloxy)phenyl, 4-bromo-3-(2-pyridyloxy)phenyl, 4-methyl-3-(2-pyridyloxy)phenyl, 4-fluoro-3-(3-pyridyloxy)phenyl, 4-chloro-3-(3-pyridyloxy)phenyl, 4-bromo-3-(3-pyridyloxy)phenyl, 4-methyl-3-(3-pyridyloxyphenyl), 2-methyl-3-phenylphenyl, 2-methyl-3-(N-pyrrolyl)phenyl, 6-phenoxy-2-pyridyl, 6-(4-fluorophenoxy)-2-pyridyl, 6-(4-chlorophenoxy)-2-pyridyl, 6-(4-bromophenoxy)-2-pyridyl, 6-(4-methylphenoxy)-2-pyridyl, 6-(4-methoxyphenoxy)-2-pyridyl, 6-(4-ethoxyphenoxy)-2-pyridyl, 6-(3-fluorophenoxy)-2-pyridyl, 6-(3-chlorophenoxy)-2-pyridyl, 6-(3-bromophenoxy)-2-pyridyl, 6-(3-methoxyphenoxy)-2-pyridyl, 6-(2-fluorophenoxy)-2-pyridyl, 6-(2-chlorophenoxy)-2-pyridyl, 6-(2-bromophenoxy)-2-pyridyl, 5-propargyl-3-furyl, N-phthalimidyl, N-3,4,5,6-phthalimidyl, 2-methyl-5-propargyl-3-furyl, 4-t-butylphenyl, 4-methylphenyl, 4-isopropylphenyl, 4-(2-chloro-4-trifluoromethyl-2-pyridyloxy)phenyl, 4-cyclohexylphenyl, 4-difluoromethoxyphenyl, 4-biphenylyl, 4-trimethylsilylphenyl and 4-phenoxy-2-thienyl.

Other typical examples of the group $$-\underset{R^4}{\underset{|}{CH}}-R^5$$

are:

2-allyl-3-methylcyclopent-2-en-1-on-4-yl, 4-phenylindan-2-yl. $R^6-R^9$ independently of one another in particular represent methyl, ethyl, propyl, iso-propyl, butyl, t-butyl, F, Cl, Br, I, vinyl, allyl, ethynyl, propargyl, methoxy, ethoxy, propoxy, iso-propoxy, difluoromethoxy, bromodifluoromethoxy, chlorodifluoromethoxy, trifluoromethoxy, 1,1,2,2-tetrafluoroethoxy, 2-chloro-1,1,2-trifluoroethoxy, 2,2,2-trifluoroethoxy, 2-fluoroethoxy, 1,1,2,3,3,3-hexafluoropropoxy, vinyloxy, allyloxy, propargyloxy, ethylthio, methylthio, propylthio, isobutylthio, trifluoromethyl, 1,1,2,2-tetrafluoroethyl, 1,1,2,2-tetrafluoroethylthio, 2,2,2-trifluoroethylthio, difluoromethylthio, trifluoromethylthio, chlorodifluoromethylthio, bromodifluoromethylthio, heptafluoropropyl, trichlorovinyl, trichlorovinyloxy, methylenedioxy or ethylenedioxy.

The present invention also relates to processes for the preparation of the compounds of the general formula (I), which comprise reacting a) a mercaptan of the general formula (II) or its salt of the general formula III $$\underset{R^3}{\underset{|}{R^1-\underset{|}{M}-CH_2-SH}} \quad \underset{R^3}{\underset{|}{R^1-\underset{|}{M}-CH_2-SM'}}$$

(II) (III)

where M' corresponds to an alkali metal equivalent or alkaline earth metal equivalent, in particular Li, Na, K, Mg, Ca, with an alkylating agent of the general formula (IV)

$$Y-\underset{R^4}{\underset{|}{CH}}-R^5 \quad \text{(IV)}$$

where Y denotes a nucleofugic leaving group, such as, for example, halogen or sulfonate, if appropriate in the presence of a base, or b) a mercaptan of the general formula (V) or its salt of the general formula (VI)

$$HS-\underset{R^4}{\underset{|}{CH}}-R^5 \quad M'-S-\underset{R^4}{\underset{|}{CH}}-R^5$$

(V) (VI)

with an alkylating agent of the general formula (VII)

$$\underset{R^3}{\underset{|}{R^1-\underset{|}{M}-CH_2-Y}} \quad \text{(VII)}$$

if appropriate in the presence of a base, or c) a sulfide of the general formula (VIII) or (IX)

$$\underset{R^3}{\underset{|}{R^1-\underset{|}{M}-CH_2-S-\underset{R^4}{\underset{|}{CH}}-Y}} \quad \underset{R^3}{\underset{|}{R^1-\underset{|}{M}-CH_2-S-\underset{Y}{\underset{|}{CH}}-R^5}}$$

(VIII) (IX)

with a metal compound of the general formula (X) or (XI)

$$M'-R^5 \quad M'-R^4$$
(X) (XI)

or—where M=Si— d) a silane of the general formula (XII)

$$\underset{R^3}{\underset{|}{R^1-\underset{|}{Si}-Y}} \quad \text{(XII)}$$

with an organometal compound of the general formula (XIII)

$$M'-CH_2-S-\underset{R^4}{\underset{|}{CH}}-R^5 \quad \text{(XIII)}$$

or—where M=Si— e) an organometal compound of the general formulae (XIV), (XV) or (XVI)

$$R^1-M' \quad R^2M' \quad R^3M'$$
(XIV) (XV) (XVI)

with a silane of the general formulae (XVII), (XVIII) or (XIX)

$$Y-\underset{R^3}{\underset{|}{Si}-CH_2-S-\underset{R^4}{\underset{|}{CH}}-R^5} \quad \text{(XVII)}$$

$$\underset{R^3}{\underset{|}{R^1-\underset{|}{Si}-CH_2-S-\underset{R^4}{\underset{|}{CH}}-R^5}} \quad \text{(XVIII)}$$

$$\underset{Y}{\underset{|}{R^1-\underset{|}{Si}-CH_2-S-\underset{R^4}{\underset{|}{CH}}-R^5}} \quad \text{(XIX)}$$

Some of the mercaptans of the general formula (II) to be used as the starting compound in preparation process a) are novel and can be prepared by a process known per se from the literature, for example by initially reacting suitable alkylating agents of the general formula (XX) (see EP-A 0,249,015 and German Patent No. 3,712,752.7)

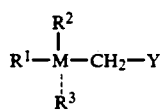

with a sulfur nucleophile, such as disulfide, thiosulfate, thioacetate or thiourea, and hydrolyzing or reducing the resulting intermediates of the general formulae (XXI), (XXII), (XXIII) or (XXIV) by customary standard methods (see also Methoden der org. Chemie [Methods of Organic Chemistry] (Houben-Weyl), Vol. E11/1, Georg Thieme Verlag, Stuttgart 1985; p. 32 et seq)

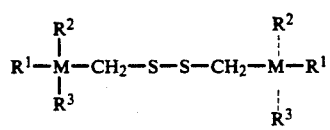

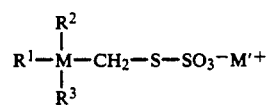

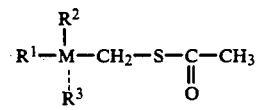

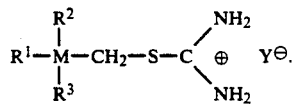

Some of the sulfides (VIII) and (IX) to be used as starting substances in preparation process c) are novel and can be prepared by a process which is known per se from the literature by reacting an alkylating agent of the general formulae (XXV) or (XXVI)

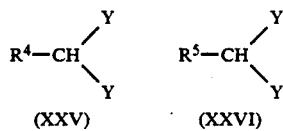

with two equivalents of a mercaptan of the formula (II) or its salt of the formula (III), if appropriate in the presence of a base, and treating the intermediates obtained, of the general formula (XXVII) or (XXVIII),

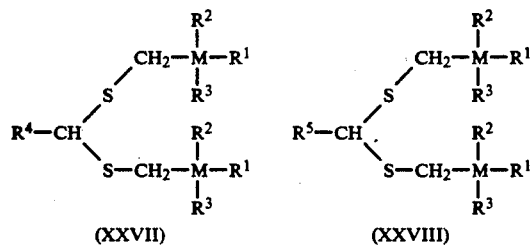

with chlorine (see Methoden der org. Chemie [Methods of Organic Chemistry] (Houben-Weyl), Vol. 5/3, Georg Thieme Verlag, Stuttgart 1962, p. 756), in which process compounds of the general formula (VIII) or (IX) where Y=Cl are formed.

In a comparable manner, chloromethyl sulfides of the general formula (XXIX) can be obtained.

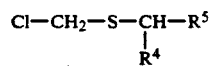

These can be used as educts for the intermediates of the general formula (XIII) which are required as a starting compound in preparation process d) and which can be prepared from them by processes known per se from the literature (see, for example, Methoden der org. Chemie [Methods of Organic Chemistry] (Houben-Weyl), Vol. 13/2a, Georg Thieme Verlag, Stuttgart 1973, p. 115).

The silanes of the general formulae (XVII), (XVIII) and (XIX) which are to be used as starting compounds in preparation process e) can be prepared by processes known per se from the literature (see Methoden der org. Chemie [Methods of Organic Chemistry] (Houben-Weyl), Vol. 13/5, Georg Thieme Verlag, Stuttgart 1980) by reacting an organometal intermediate of the general formula (XIII) with silanes of the formulae (XXX), (XXXI) or (XXXII)

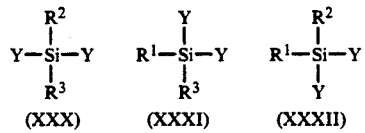

The intermediates (IV), (V), (VI), (VII), (X), (XI), (XII), (XIV), (XV) and (XVI) are either obtained as described above (EP-A 0,249,015 and German Patent No. 3,712,752.7), or alternatively they can be prepared by methods quoted in the current literature (see, inter alia, the literature quoted so far).

The mentioned process variants c), d) and e) are preferably carried out in a diluent the nature of which depends on the type of the organometal compound employed. Suitable diluents are, in particular, aliphatic and aromatic hydrocarbons, such as, for example, pentane, hexane, heptane, cyclohexane, petroleum ether, benzine, ligroin, benzene, toluene and xylene, ethers, such as, for example, diethyl ether, dibutyl ether, glycol dimethyl ether, diglycol dimethyl ether, tetrahydrofuran or dioxane, and, finally, all possible mixtures of the previously mentioned solvents.

In the abovementioned process variants, the reaction temperature is between −110° C. and +150° C., preferably between −75° C. and +105° C. The starting materials are usually employed in equimolar amounts. However, it is possible to use an excess of one or the other reactant.

What has been said for variants c)–e) is essentially also true for process variants a) and b) which have been mentioned further above. Alternatively, other diluents can be used. Thus, in these cases, alcohols, such as, for example, methanol, ethanol, propanol, i-propanol or butanol, amides, such as, for example, dimethylformamide, dimethylacetamide or N-methylpyrrolidone, nitriles, such as, for example, acetonitrile or butyronitrile, ketones, such as, for example, acetone or MIBK, and also dimethyl sulfoxide, tetramethylene sulfone or hexamethylphosphoric triamide are also suitable as diluents. However, process variants a) and b) can also be carried out without diluents.

Bases which can be used are inorganic bases, such as, for example, the hydroxides, hydrides, carbonates, acetates or hydrogen carbonates of alkali metals and alkaline earth metals, but also organic bases, such as, for example, pyridine, triethylamine, N,N-diisopropylethylamine or diazabicyclooctane. The mercaptans (II) or (V) can alternatively be converted to their salts (III) or (VI), respectively, by adding organometal reagents, such as, for example, methyllithium, butyllithium, methylmagnesium halide, phenylmagnesium halide etc.

The compounds of the formula (I) are isolated, and, if appropriate, purified by generally customary methods, for example by distilling of the solvent (if appropriate under reduced pressure), followed by distillation chromatography or distribution of the crude product between two phases and its subsequent customary work-up.

The compounds of the general formula (I) are readily soluble in most organic solvents.

The active compounds are well tolerated by plants, have a favourable toxicity to warm-blooded animals and are suitable for combating animal pests, in particular insects, arachnids and nematodes, which are encountered in agriculture, in forestry, in the protection of stored products and of materials, and in the hygiene field. They are active against normally sensitive and resistant species and against all or individual stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratoriodes, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hypalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypielle, Bupalus piniarius, Cheimatobia brumata, Lithocolletis blancardella, Hyponomeuta padella, Plutella maculipennis, Malcosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Caprocapsa pomonella,* Pieris spp., Chilo spp., *Pyrausta nubilalis, Ephestia koehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomya hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

Furthermore the compounds have an excellent action against Nematodes which are harmful to plant, for example those of the species Meloidogyne, Heterodera, Ditylenchus, Aphelenchoides, Radopholus, Globodera, Pratylenchus, Longidorus and Xiphinema.

The invention also relates to agents which contain the compounds of the formula (I) besides suitable formulation auxiliaries. In general, the agents according to the invention contain 1–95% by weight of the active substances of the formula (I). They can be formulated in different ways, depending on the biological and/or chemical-physical parameters. Thus, the following formulation possibilities are suitable: wettable powders (WP), emulsifiable concentrates (EC), aqueous solutions (SC), emulsions, spraying solutions, dispersions on oil or water bases (SC), suspo emulsions (SC), dusting agents (DA), dressing agents, granules in the form of microgranules, sprayable granules, coated granules and adsorption granules, water-dispersable granules (WG), ULV formulations, microcapsules, waxes or baits.

These individual formulation types are known in principle and are described, for example, in: Winnacker- Kuchler, "Chemische Technologie [Chemical Technology]", Volume 7, C. Hauser Verlag Munich, 4th edition 1986; van Falkenberg, "Pesticides Formulations", Marcel Dekker New York, 2nd Ed. 1972-73; K. Martens, "Spray Drying Handbook", 3rd Ed. 1979, G. Goodwin Ltd, London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldwell, N.J.; H. v. Olphen, "Introduction to Clay Colloid Chemistry", 2nd Ed., J. Wiley & Sons, New York; Marschen, "Solvents Guide", 2nd Ed., Interscience, New York 1950; McCutcheon's, "Detergents and Emulsifiers Annual", MC Publ. Corp., Ridgewood, N.J.; Sisley and Wood, "Encyclopedia of Surface Active Agents", Chem. Publ. Co. Inc., New York 1964; Schönfeldt, "Grenzflächenaktive Äthylenoxidaddukte [Surface-active ethylene oxide adducts]", Wiss. Verlagsgesell., Stuttgart 1976; Winnacker-Küchler, "Chemische Technologie [Chemical Technology]", Volume 7, C. Hauser Verlag Munich, 4th edition 1986.

On the basis of these formulations, it is also possible to prepare combinations with other pesticidally active substances, fertilizers and/or growth regulators, for example in the form of a readymix or as a tank mix. Wettable powders are preparations, uniformly dispersable in water, which contain, besides the active substance and in addition to a diluent or inert substance, wetting agents, for example polyoxyethylated alkylphenols, polyoxyethylated fatty alcohols, alkyl- or alkylphenol sulfonates, and dispersing agents, for example sodium ligninsulfonate, sodium 2,2'-dinaphthylmethane-6,6'-disulfonate, sodium dibutylnaphthalenesulfonate, or sodium oleoylmethyltaurinate. Emulsifiable concentrates are prepared by dissolving the active substance in an organic solvent, for example butanol, cyclohexanone, dimethylformamide, xylene or higher-boiling aromatics or hydrocarbons, with the addition of one or more emulsifiers. Examples of emulsifiers which can be used are: calcium salts of alkylarylsulfonate, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyether, sorbitan fatty acid esters, polyoxyethylene sorbitan fatty acid esters or polyoxyethylene sorbitol esters.

Dusting agents are obtained by grinding the active compound with finely divided solid substances, for example talc, natural clays such as kaolin, bentonite, pyrophillite or diatomaceous earth. Granules can be prepared either by atomizing the active substance onto adsorptive, granulated inert material or by applying active compound concentrates onto the surface of carrier materials, such as sand, kaolinites or granulated inert material, by means of adhesives, for example polyvinyl alcohol or sodium polyacrylate, or alternatively mineral oils. Suitable active substances can also be granulated in the manner customary for the preparation of fertilizer granules—if desired as a mixture with fertilizers.

In wettable powders, the active substance concentration is, for example, approximately 10 to 90% by weight, the remainder to 100% by weight consists of customary formulation components. In the case of emulsifiable concentrates, the active substance concentration may be approximately 5 to 80% by weight. Formulations in the form of dusts usually contain 5 to 20% by weight of active substance, sprayable solutions approximately 2 to 20% by weight. In the case of granules, the active substance content partly depends on whether the active substance is present as a liquid or as a solid, and which granulation auxiliaries, fillers etc. are used.

Besides, the active substance formulations mentioned may contain the adhesives, wetting agents, dispersing agents, emulsifiers, penetrants, solvents, fillers or carriers which are customary in each case.

For application the concentrates present in commercially available form may be diluted in a customary manner, for example in the case of wettable powders, emulsifiable concentrates, dispersions and, in some cases, also in the case of microgranules, by means of water. Preparations in the form of dusts and of granules and also sprayable solutions are usually not diluted any further with other inert substances prior to application.

The dosage rate required varies with the external conditions, such as temperature, humidity and the like. It can vary within wide limits, for example between 0.005 and 10.0 kg/ha or more of active substance, however, preferably it is between 0.01 and 5 kg/ha.

The active substances according to the invention can be present in their commercially available formulations and in the application forms prepared form these formulations, in mixtures with other active substances, such as insecticides, pheromones, sterilants, acaricides, nematicides, fungicides, growth-regulating substances or herbicides.

The insecticides include, for example, phosphoric acid esters, carbamates, carboxylic acid esters, formamidines, tin-compounds, substances prepared by microorganisms and the like.

Preferred mixture components are 1. from the group comprising the phosphorus compounds acephate, azamethiphos, azinphos-ethyl, azinphos-methyl, bromophos, bromophos-ethyl, chlorfenvinphos, chlormephos, chlorpyrifos, chlorpyriphos-methyl, demeton, demeton-S-methyl, demeton-S-methyl sulfphone, dialifos, diazinon, dichlorvos, dicrotophos, 0,0-1,2,2,2-tetrachlorethylphosphorthioate (SD 208 304), dimethoate, disulfoton, EPN, ethion, ethoprophos, etrimfos, famphur, fenamiphos, fenitrothion, fensulfothion, fenthion, fonofos, formothion, heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetraclorvinphos, thiometon, triazophos, trichlorphon, vamidothion;

2. from the group comprising the carbamates aldicarb, 2-sec.-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cu menylbutyryl(methyl)carbamate, oxamyl, pirimicarb, propoxur, thiodicarb, thiofanox, ethyl 4,6,9-triaza-4-benzyl-6,10-dimethyl-8-oxa-7-oxa-5,11-dithia-9-dodecenoate (OK 135), 1-methylthio(ethylideneamino) N-methyl-N-(morpholinothio)carbamate (UC 51717);

3. from the group comprising the carboxylic acid esters allethrin, alphametrin, 5-benzyl-3-furylmethyl (E)-(1R)-cis-2,2-dimethyl-3-(2-oxothiolan-3-ylidenemethyl) cyclopropanecarboxylate, bioallethrin, bioallethrin((S)-cyclopentylisomer), bioresmethrin, biphenate, (RS)-1-cyano-1-(6-phenoxy-2-pyridyl)-methyl (1RS)-trans-3-(4-tert.butylphenyl)-2,2-dimethyl-cyclopropanecarboxylate (NCI 85193), cycloprothrin, cyfluthrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D-isomer), permethrin, phenothrin ((R)-isomer), d-pralethrin, pyrethrins (natural products), resmethrin, tefluthrin, tetramethrin, tralomethrin, hydroprene, methoprene, kinoprene; 4. from the group comprising the amidines amitraz, chlordimeform;

5. from the group comprising the tin compounds cyhexatin, fenbutatin oxides, azocyclotin;

6. others abamectin, Bacillus thuringiensis, bensultrap, binapacryl, bromopropylate, buprofezin, camphechlor, cartap, chlorobenzilate, chlorfluazuron, 2-(4-chlorophenyl)-4,5-diphenylthiophene (UBI-T 930), chlorofentezine, 2-naphthylmethyl cyclopropanecarboxylate (Ro 12-0470), cyromazin, N-(3,5-dichloro-4-(1,1,2,3,3,3-hexafluoro-1-propyloxy)phenyl)carbamoyl)-2-chlorobenzocarboximidate, DDT, dicofol, N-(N-(3,5-dichloro-4-(1,1,2,2-tetrafluoroethoxy)-phenylamino)carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox. (4-ethoxyphenyl)(dimethyl)(3-(3-phenoxyphenyl)propyl)silane, (4-ethoxyphenyl)(3-(4-fluoro-3-phenoxyphenyl)propyl)dimethylsilan, fenoxycarb, 2-fluoro-5-(4-(4-ethoxyphenyl)-4-methyl-1-pentyl)diphenyl ether (MTI 800), granulosis and nuclear polyhedrosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro-6H-thiazine (SD 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, triflumuron, O-ethyl-N-[2-(4-phenoxy)-phenoxyethyl]carbamate, O-[2-(4-phenoxy)phenoxyethyl]propionaldoxim, 1-(4-phenoxy-phenoxy)-2-(2-pyridinoxy)propane.

The active substance content of the use forms prepared from the commercially available formulations can very within broad ranges. The active substance concentration of the use forms can be from 0.0000001 to 100% by weight of active substance, preferably between 0.00001 and 1% by weight. Application is effected in a conventional fashion, matched to the use forms.

The active substances according to the invention are also suitable for combating ecto- and endoparasites, preferably ectoparasitizing insects, in the veterinary medicine area or in the area of animal husbandry.

The active substances according to the invention are applied here in a known fashion, such as by oral application in the form of, for example, tablets, capsules, potions or granules, by dermal application in the form of, for example, dipping, spraying, pouring-on and spotting-on and powdering.

The dosages and formulations suitable in each case are particularly dependent on the type and stage of development of the productive animals and also on the degree of infestation of the insects, and can easily be determined and fixed by conventional methods.

The following examples serve to illustrate the invention.

A. FORMULATION EXAMPLES a) A dusting agent is obtained by mixing 10 parts by weight of active substance and 90 parts by weight of talc as inert material and comminuting in a hammer mill.

b) A wettable powder which is easily dispersible in water is obtained by mixing 25 parts by weight of active substance, 65 parts by weight of kaolin-containing quartz as inert material, 10 parts by weight of potassium ligninsulfonate and 1 part by weight of sodium oleoylmethyltaurinate as wetting and dispersing agent, and grinding in a pin disk mill.

c) A dispersion concentrate which is easily dispersible in water is prepared by mixing 40 parts by weight of active compound with 7 parts by weight of a sulfo succinic acid monoester, 2 parts by weight of the sodium salt of a ligninsulfonate and 51 parts by weight of water and grinding in a ball mill to a fineness of below 5 microns.

d) An eumlsifiable concentrate can be prepared from 15 parts by weight of active substance, 75 parts by weight of cyclohexanone as solvent and 10 parts by weight of oxyethylated nonylphenol (10 EO) as emulsifier.

e) Granules can be prepared from 2 to 15 parts by weight of active substance and an inert granule carrier material, such as attapulgite, pumice granules and/or quartz sand. A suspension of the wettable powder from example b), having a solids content of 30% is expediently used, and this is sprayed onto the surface of attapulgite granules, which are dried and mixed intimately. Here, the proportion by weight of the wettable powder is approx. 5% and that of the inert carrier material approx. 95% of the finished granules.

B. CHEMICAL EXAMPLES

Preparation Instructions 1) 56 ml (=140 mmol) of 2.5 M-n-butyllithium solution in hexane are added dropwise at −70° C. to a mixture of 25.6 g (100 mmol) of 5-bromo-2-(2,2,2-trifluoro ethoxy)pyridine (from 2,5-dibromopyridine and 2,2,2-trifluoroethanol/sodium hydride in DMSO), 20 g (140 mmol) of chloro-chloromethyl-dimethylsilane and 120 ml of anhydrous tetrahydrofuran. After the addition is complete, stirring is continued for a further 30 minutes at −70° C., the reaction mixture is allowed to slowly come to room temperature, and 5 ml of water are finally added. After the reaction solution has been evaporated, the residue is taken up in 200 ml of hexane, and the mixture is washed twice using water. The hexane phase, which has been dried over $Na_2SO_4$, contains butylchloromethyldimethylsilane as a by-product, besides the desired intermediate <2-(2,2,2-trifluoroethoxy)pyrid-5-yl)-(dimethyl)-(chloromethyl)-silane.

Most of the by-product is removed by incipient distillation of the crude product at up to 50° C. (internal temperature) at 0.2 mbar. The silylpyridine, which remains in the residue, is added dropwise without further purification at room temperature to a solution of 15 g (130 mmol) of potassium thio acetate in 100 ml of anhydrous DMSO. The reaction mixture is allowed to stand at 60°-70° C. for 1.5 h and is then poured into 1 l of ice water, and the product is extracted using several portions of ether. The extracts are washed three times using a 20% strength sodium chloride solution, dried over $Na_2SO_4$ and evaporated. Subsequent distillation in vacuo yields 22.3 g (69%) of <2-(2,2,2-trifluoroethoxy)-pyrid-5yl>-(dimethyl)-(acetylthiomethyl)silane as a pale yellow oil of boiling point 95°-100° C./0.1 mbar.

2) The solution of 22.3 g (69 mmol) of <2-(2,2,2-trifluoroethoxy)-pyrid-5-yl>-(dimethyl)-(acetylthiomethyl)-silane in 200 ml of anhydrous ether is added dropwise at room temperature to a stirred suspension of 5.3 g (140 mmol) of lithiumaluminum hydride in 50 ml of anhydrous ether. After a further 3 h, the reaction mixture is decomposed by the dropwise addition of a little water. The solid precipitate which forms during this process is filtered off with suction and washed thoroughly using ether. After evaporation, the filtrates yield 8.6 g (44%) of (mercaptomethyl)-(dimethyl)-<2-(2,2,2-trifluoroethoxy)-pyrid-5-yl)-silane as a pale yellow oil.

3) At −60° C., initially the solution of 4.3 g (15.3 mmol) of (mercaptomethyl)-(dimethyl)-<2-(2,2,2-trifluoroethyoxy)-pyrid-5-yl>silane in 10 ml of THF and then 10 ml of 1.6M-methyllithium solution in ether are added dropwise to a solution of 5.3 g (18.8 mmol) of 4-fluoro-3-phenoxybenzyl bromide in 10 ml of anhydrous THF. During a subsequent period of approximately 2 hours, the reaction solution is allowed to come to room temperature, and stirring is continued for 2 hours at 20°-25° C. After the addition of 200 ml of water, the product is extracted using two 100 ml portions of hexane. After the extracts have been washed twice using water, dried ($Na_2SO_4$) and evaporated 8.1 g of crude product are obtained. Through subsequent chromatography of silica gel using methylene chloride/hexane (1:1), 3.1 g (42%) of (dimethyl)<2-(2,2,2-trifluoroethoxy)-pyrid-5-yl>-<(4-fluoro-3-phenoxy-benzyl)-thiomethyl>silane (Example 26/Table 1) of a pale yellow oil of boiling point $_{0.05}$=230°-240° C. (bulb tube) are obtained. In analogy to these constructions, the compounds listed below, where M=Si, can be prepared. The syntheses of the compounds below, where M=C, proceed entirely analogously with respect to their steps 2) and 3). The preparation of the carbon compounds which are analogous to the product of step 1) is described in German Patent 3,712,752.7.

TABLE 1

$$R^1-\underset{\underset{R^3}{|}}{\overset{\overset{R^2}{|}}{M}}-CH_2-S-\underset{\underset{R^4}{|}}{CH}-R^5 \quad (1)$$

M = Si: $R^2 = R^3 = CH_3$

| No. | $R^1$ | $R^4$ | $R^5$ | Physical data |
|---|---|---|---|---|
| 1 | EtO-[pyridyl] | H | [phenoxyphenyl] | b.p.$_{0.1}$ = 240° C. |
| 2 | " | H | [phenoxy-fluorophenyl] | b.p.$_{0.03}$ = 235-240° C. |
| 3 | " | H | [fluoro-(fluorophenoxy)phenyl] | |
| 4 | " | H | [pyridyl-O-phenyl] | b.p.$_{0.2}$ = 245-250° C. |
| 5 | " | H | [thiophene-O-phenyl] | b.p.$_{0.1}$ = 235-245° C. |

TABLE 1-continued $$R^1-M(R^2)(R^3)-CH_2-S-CH(R^4)-R^5 \quad (1)$$

M = Si; $R^2 = R^3 = CH_3$

| No. | $R^1$ | $R^4$ | $R^5$ | Physical data |
|---|---|---|---|---|
| 6 | | CN | 3-phenoxyphenyl | highly viscous oil |
| 7 | 2-methoxypyridin-5-yl | H | 3-phenoxyphenyl | |
| 8 | " | H | 2-fluoro-3-phenoxyphenyl (via O) | b.p.$_{0.2}$ = 240–245° C. |
| 9 | " | H | 2-(4-fluorophenoxy)-fluorophenyl | |
| 10 | " | H | pyridin-2-yloxy-phenyl | |
| 11 | " | H | thiophen-3-yl phenoxy | b.p.$_{0.05}$ = 235–245° C. |
| 12 | " | CN | 3-phenoxyphenyl | |
| 13 | 2-chloropyridin-5-yl | H | 3-phenoxyphenyl | |

TABLE 1-continued $$R^1-\underset{\underset{R^3}{|}}{\overset{\overset{R^2}{|}}{M}}-CH_2-S-\underset{\underset{R^4}{|}}{CH}-R^5 \qquad (1)$$

M = Si: $R^2 = R^3 = CH_3$

| No. | $R^1$ | $R^4$ | $R^5$ | Physical data |
|---|---|---|---|---|
| 14 | " | H | ⟨aryl-F with OPh⟩ | b.p._{0.01} = 220–225° C. |
| 15 | " | H | ⟨aryl-F with O-C6H4-F⟩ | |
| 16 | " | H | ⟨pyridyl-O-Ph⟩ | |
| 17 | " | H | ⟨thienyl-O-Ph⟩ | b.p._{0.07} = 230° C. |
| 18 | " | CN | ⟨aryl-O-Ph⟩ | |
| 19 | ⟨methylenedioxy-tetrahydropyridinyl⟩ | H | ⟨aryl-O-Ph⟩ | b.p._{0.1} = 230–235° C. |
| 20 | " | H | ⟨aryl-F with O-Ph⟩ | b.p._{0.05} = 230–240° C. |
| 21 | " | H | ⟨aryl-F with O-C6H4-F⟩ | |

TABLE 1-continued $$R^1-\underset{\underset{R^3}{|}}{\overset{\overset{R^2}{|}}{M}}-CH_2-S-\underset{\underset{R^4}{|}}{\overset{}{CH}}-R^5 \quad (1)$$

M = Si: R² = R³ = CH₃

| No. | R¹ | R⁴ | R⁵ | Physical data |
|---|---|---|---|---|
| 22 | " | H | (6-methylpyridin-2-yl)oxyphenyl | b.p.₀.₀₂ = 240–250° C. |
| 23 | " | H | (thiophen-3-yl)oxyphenyl | |
| 24 | " | CN | phenoxyphenyl | |
| 25 | F₃C—CH₂—O-pyridinyl | H | phenoxyphenyl | b.p.₀.₂ = 245° C. |
| 26 | " | H | fluoro-phenoxyphenyl | b.p.₀.₀₅ = 230–240° C. |
| 27 | " | H | fluoro-phenoxy-(4-fluorophenyl) | |
| 28 | " | H | (6-methylpyridin-2-yl)oxyphenyl | |
| 29 | " | H | (thiophen-3-yl)oxyphenyl | b.p.₀.₀₅ = 230–240° C. |

TABLE 1-continued
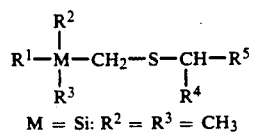
M = Si: R² = R³ = CH₃
| No. | R¹ | R⁴ | R⁵ | Physical data |
|-----|----|----|----|---------------|
| 30 | " | CN | phenyl-O-phenyl | |
| 31 | F—CH₂—CH₂—O-pyridinyl- | H | phenyl-O-phenyl | |
| 32 | " | H | (F-phenyl)-O-phenyl | b.p.$_{0.07}$ = 235° C. |
| 33 | " | H | (F-phenyl)-O-(F-phenyl) | |
| 34 | " | H | pyridinyl-O-phenyl | |
| 35 | " | H | thienyl-O-phenyl | |
| 36 | " | CN | phenyl-O-phenyl | |
| 37 | EtS-pyridinyl- | H | phenyl-O-phenyl | b.p.$_{0.05}$ = 240–245° C. |

TABLE 1-continued $$R^1-\underset{\underset{R^3}{|}}{\overset{\overset{R^2}{|}}{M}}-CH_2-S-\underset{\underset{R^4}{|}}{CH}-R^5 \quad (1)$$

M = Si: $R^2 = R^3 = CH_3$

| No. | $R^1$ | $R^4$ | $R^5$ | Physical data |
|---|---|---|---|---|
| 38 | " | H | (3-methyl-2-fluorophenyl)-O-phenyl | b.p.$_{0.01}$ = 235–240° C. |
| 39 | " | H | (3-methyl-2-fluorophenyl)-O-(4-fluorophenyl) | |
| 40 | " | H | (6-methylpyridin-2-yl)-O-phenyl | |
| 41 | " | H | (5-methylthiophen-3-yl)-O-phenyl | |
| 42 | " | CN | (3-methylphenyl)-O-phenyl | |
| 43 | $F_3C-CH_2-S-$(5-methylpyridin-2-yl) | H | (3-methylphenyl)-O-phenyl | |
| 44 | " | H | (3-methyl-2-fluorophenyl)-O-phenyl | |
| 45 | " | H | (3-methyl-2-fluorophenyl)-O-(4-fluorophenyl) | |

TABLE 1-continued
$$R^1-\underset{\underset{R^3}{|}}{\overset{\overset{R^2}{|}}{M}}-CH_2-S-\underset{\underset{R^4}{|}}{CH}-R^5 \quad (1)$$
M = Si: $R^2 = R^3 = CH_3$
| No. | $R^1$ | $R^4$ | $R^5$ | Physical data |
|---|---|---|---|---|
| 46 | " | H | 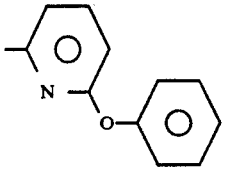 | |
| 47 | " | H | 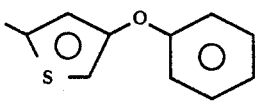 | |
| 48 | " | CN | 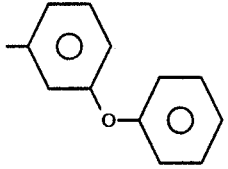 | |
| 49 | 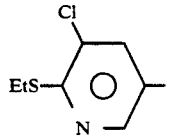 | H | 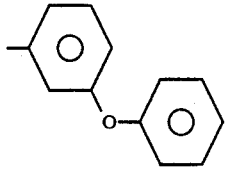 | |
| 50 | " | H | 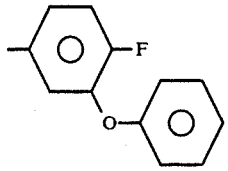 | b.p.$_{0.05}$ > 250° C. |
| 51 | " | H | 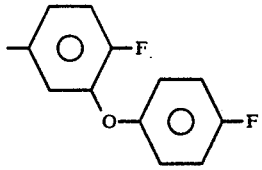 | |
| 52 | " | H | 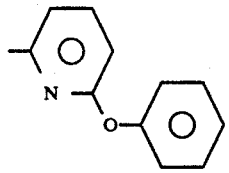 | |
| 53 | " | H | 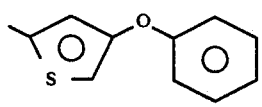 | |

TABLE 1-continued $$R^1-\underset{\underset{R^3}{|}}{\overset{\overset{R^2}{|}}{M}}-CH_2-S-\underset{\underset{R^4}{|}}{CH}-R^5 \quad (1)$$

M = Si: $R^2 = R^3 = CH_3$

| No. | $R^1$ | $R^4$ | $R^5$ | Physical data |
|---|---|---|---|---|
| 54 | " | CN | 3-phenoxyphenyl | |
| 55 | 3-chloro-2-ethoxy-pyridin-5-yl | H | 3-phenoxyphenyl | b.p.$_{0.01}$ = 250° C. |
| 56 | " | H | 2-fluoro-3-phenoxyphenyl | b.p.$_{0.01}$ = 250° C. |
| 57 | " | H | 2-fluoro-3-(4-fluorophenoxy)phenyl | |
| 58 | " | H | 6-phenoxypyridin-2-yl | |
| 59 | " | H | 4-phenoxythiophen-2-yl | |
| 60 | " | CN | 3-phenoxyphenyl | |
| 61 | 2,3-dichloro-pyridin-5-yl | H | 3-phenoxyphenyl | b.p.$_{0.05}$ = 240–245° C. |

TABLE 1-continued
$$R^1-\underset{\underset{R^3}{|}}{\overset{\overset{R^2}{|}}{M}}-CH_2-S-\underset{\underset{R^4}{|}}{CH}-R^5 \quad (1)$$
M = Si; R² = R³ = CH₃
| No. | R¹ | R⁴ | R⁵ | Physical data |
|---|---|---|---|---|
| 62 | " | H | 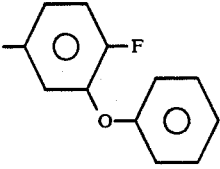 | b.p.·0.03 = 240–245° C. |
| 63 | " | H | 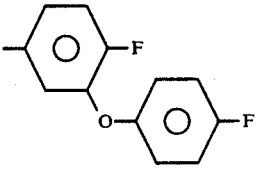 | b.p.·0.05 = 240–245° C. |
| 64 | " | H | 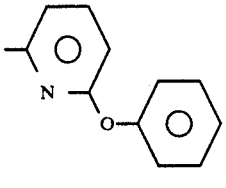 | |
| 65 | " | H |  | b.p.·0.05 = 240° C. |
| 66 | " | CN | 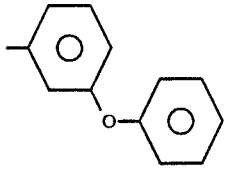 | |
| 67 | 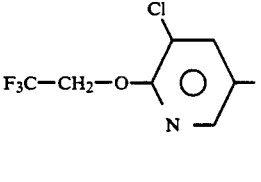 | H | 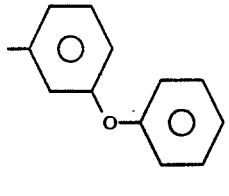 | b.p.·0.05 = 250° C. |
| 68 | " | H | 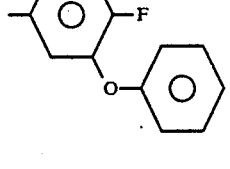 | b.p.·0.02 = 250° C. |
| 69 | " | H | 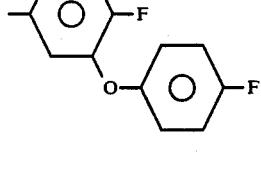 | |

TABLE 1-continued
$$R^1-\underset{\underset{R^3}{\overset{\overset{R^2}{|}}{M}}}{}-CH_2-S-\underset{\underset{R^4}{|}}{CH}-R^5 \quad (1)$$
M = Si: $R^2 = R^3 = CH_3$
| No. | $R^1$ | $R^4$ | $R^5$ | Physical data |
|---|---|---|---|---|
| 70 | " | H | 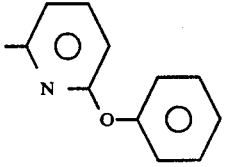 | |
| 71 | " | H | 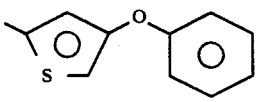 | |
| 72 | " | CN | 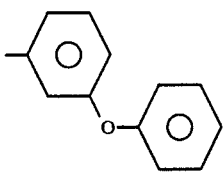 | |
| 73 | 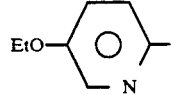 | H | 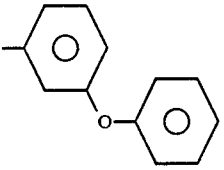 | |
| 74 | " | H | 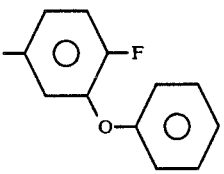 | b.p.$_{0.01}$ = 240–245° C. |
| 75 | " | H | 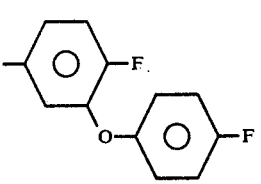 | |
| 76 | " | H | 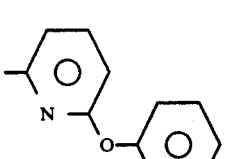 | |
| 77 | " | H | 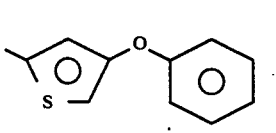 | |

TABLE 1-continued $$R^1-M(R^2)(R^3)-CH_2-S-CH(R^4)-R^5 \quad (1)$$

M = Si; R² = R³ = CH₃

| No. | R¹ | R⁴ | R⁵ | Physical data |
|---|---|---|---|---|
| 78 | " | CN | 3-phenoxyphenyl | |
| 79 | 5-chloro-2-pyridyl | H | 3-phenoxyphenyl | |
| 80 | " | H | 2-fluoro-3-phenoxyphenyl | b.p.₀.₀₅ = 230–235° C. |
| 81 | " | H | 2-fluoro-3-(4-fluorophenoxy)phenyl | |
| 82 | " | H | 6-phenoxy-2-pyridyl | |
| 83 | " | H | 4-phenoxy-2-thienyl | |
| 84 | " | CN | 3-phenoxyphenyl | |
| 85 | 5-methyl-2-pyridyl | H | 3-phenoxyphenyl | b.p.₀.₀₂ = 240° C. |

TABLE 1-continued $$R^1-\underset{\underset{R^3}{|}}{\overset{\overset{R^2}{|}}{M}}-CH_2-S-\underset{\underset{R^4}{|}}{CH}-R^5 \quad (1)$$

M = Si: R² = R³ = CH₃

| No. | R¹ | R⁴ | R⁵ | Physical data |
|---|---|---|---|---|
| 86 | " | H | (3-phenoxy-2-fluorophenyl) | |
| 87 | " | H | (3-(4-fluorophenoxy)-2-fluorophenyl) | |
| 88 | " | H | (6-phenoxypyridin-2-yl) | |
| 89 | " | H | (5-methyl-3-phenoxythiophen-2-yl) | |
| 90 | " | CN | (3-phenoxyphenyl) | |
| 91 | (5-bromopyridin-2-yl) | H | (3-phenoxyphenyl) | b.p.₀.₀₂ = 235–240° C. |
| 92 | " | H | (3-phenoxy-2-fluorophenyl) | |
| 93 | " | H | (3-(4-fluorophenoxy)-2-fluorophenyl) | |

TABLE 1-continued $$R^1-M(R^2)(R^3)-CH_2-S-CH(R^4)-R^5 \quad (1)$$

M = Si; $R^2 = R^3 = CH_3$

| No. | $R^1$ | $R^4$ | $R^5$ | Physical data |
|---|---|---|---|---|
| 94 | " | H | [6-methylpyridin-2-yl phenyl ether] | |
| 95 | " | H | [5-methylthiophen-3-yl phenyl ether] | |
| 96 | " | CN | [3-methylphenyl phenyl ether] | |
| 97 | 2-ethoxypyrimidin-5-yl | H | [3-methylphenyl phenyl ether] | pale yellow oil $R_f(CH_2Cl_2/\text{heptane } 4:1) = 0.25$ |
| 98 | " | H | [4-methyl-2-fluorophenyl phenyl ether] | pale yellow oil $R_f(CH_2Cl_2/\text{heptane } 4:1) = 0.25$ |
| 99 | " | H | [4-methyl-2-fluorophenyl 4-fluorophenyl ether] | |
| 100 | " | H | [6-methylpyridin-2-yl phenyl ether] | |
| 101 | " | H | [5-methylthiophen-3-yl phenyl ether] | |

TABLE 1-continued $$R^1-\underset{\underset{R^3}{|}}{\overset{\overset{R^2}{|}}{M}}-CH_2-S-\underset{\underset{R^4}{|}}{CH}-R^5 \quad (1)$$

M = Si: R² = R³ = CH₃

| No. | R¹ | R⁴ | R⁵ | Physical data |
|---|---|---|---|---|
| 102 | " | CN | 3-phenoxyphenyl | |
| 103 | 2-(ethylthio)pyrimidin-5-yl | H | 3-phenoxyphenyl | |
| 104 | " | H | 3-phenoxy-2-fluorophenyl | |
| 105 | " | H | 3-(4-fluorophenoxy)-2-fluorophenyl | |
| 106 | " | H | 6-phenoxypyridin-2-yl | |
| 107 | " | H | 3-phenoxythien-2-yl | |
| 108 | " | CN | 3-phenoxyphenyl | |
| 109 | 2-(2,2,2-trifluoroethoxy)pyrimidin-5-yl | H | 3-phenoxyphenyl | pale yellow oil R$_f$(CH₂Cl₂) = 0.3 |

TABLE 1-continued
$$R^1-\underset{\underset{R^3}{|}}{\overset{\overset{R^2}{|}}{M}}-CH_2-S-\underset{\underset{R^4}{|}}{CH}-R^5 \quad (1)$$
M = Si: R² = R³ = CH₃
| No. | R¹ | R⁴ | R⁵ | Physical data |
|---|---|---|---|---|
| 110 | " | H | 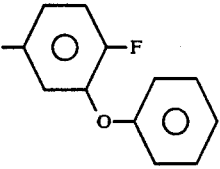 | pale yellow oil R_f(CH₂Cl₂) = 0.3 |
| 111 | " | H | 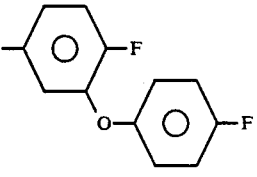 | |
| 112 | " | H | 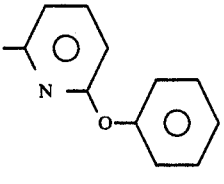 | |
| 113 | " | H | 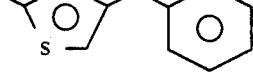 | |
| 114 | " | CN | 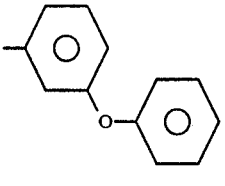 | |
| 115 | F—CH₂—CH₂—O—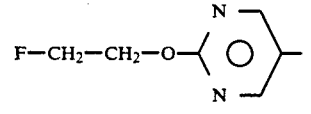 | H | 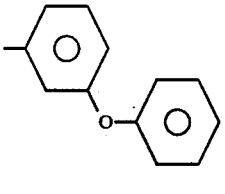 | |
| 116 | " | H | 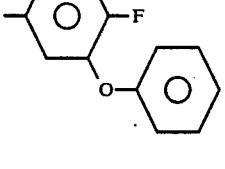 | |
| 117 | " | H | 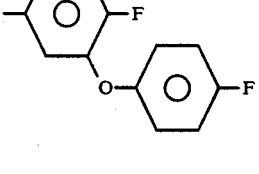 | |

TABLE 1-continued
$$R^1-\underset{\underset{R^3}{|}}{\overset{\overset{R^2}{|}}{M}}-CH_2-S-\underset{\underset{R^4}{|}}{CH}-R^5 \quad (1)$$
M = Si: $R^2 = R^3 = CH_3$
| No. | $R^1$ | $R^4$ | $R^5$ | Physical data |
|---|---|---|---|---|
| 118 | " | H | 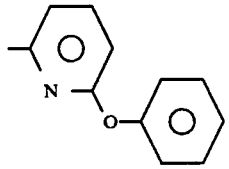 | |
| 119 | " | H | 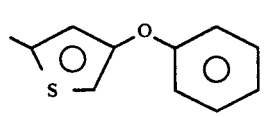 | |
| 120 | " | CN | 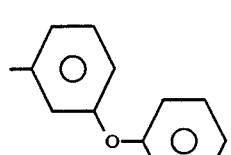 | |
| 121 | 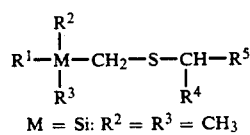 | H | 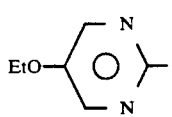 | |
| 122 | " | H | 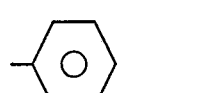 | |
| 123 | " | H | 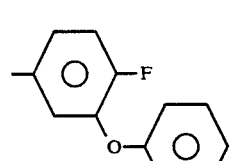 | |
| 124 | " | H | 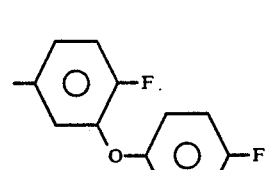 | |
| 125 | " | H | 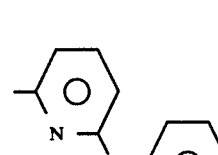 | |

TABLE 1-continued $$R^1-\underset{\underset{R^3}{|}}{\overset{\overset{R^2}{|}}{M}}-CH_2-S-\underset{\underset{R^4}{|}}{CH}-R^5 \quad (1)$$

M = Si: R² = R³ = CH₃

| No. | R¹ | R⁴ | R⁵ | Physical data |
|---|---|---|---|---|
| 126 | " | CN | —⌬—O—⌬ | |
| 127 | EtS-[pyrimidine]- | H | —⌬—O—⌬ | |
| 128 | " | H | —⌬(F)—O—⌬ | |
| 129 | " | H | —⌬(F)—O—⌬—F | |
| 130 | " | H | —[pyridine]—O—⌬ | |
| 131 | " | H | —[thiophene]—O—⌬ | |
| 132 | " | CN | —⌬—O—⌬ | |

TABLE 2
M = C; R² = R³ = CH₃
| No. | R¹ | R⁴ | R⁵ | Physical data |
|-----|----|----|----|---------------|
| 133 | 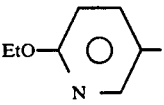 | H | 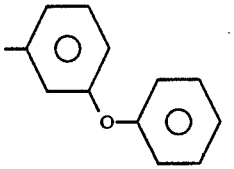 | b.p.$_{0.001}$ = 224–230° C. |
| 134 | " | H | 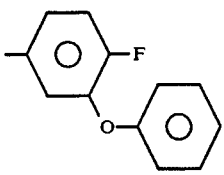 | b.p.$_{0.05}$ = 230–235° C. |
| 135 | " | H | 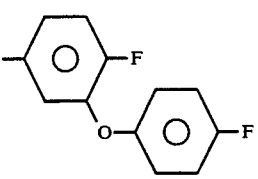 | |
| 136 | " | H | 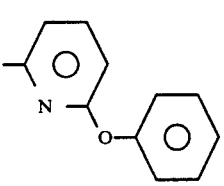 | |
| 137 | " | H | 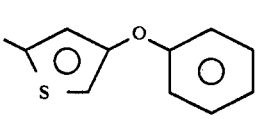 | b.p.$_{0.0005}$ = 210° C.<br>b.p.$_{0.01}$ = 220–230° C. |
| 138 | " | CN | 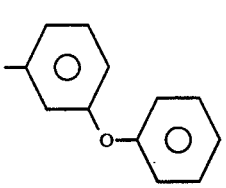 | |
| 139 | 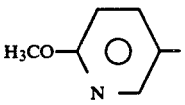 | H | 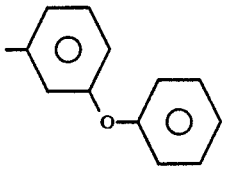 | |
| 140 | " | H | 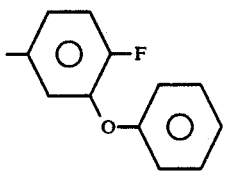 | |

TABLE 2-continued
| No. | R¹ | M = C; R² = R³ = CH₃ | | Physical data |
|---|---|---|---|---|
| | | R⁴ | R⁵ | |
| 141 | " | H | 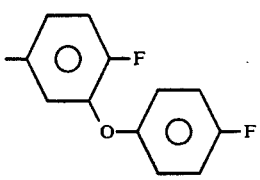 | |
| 142 | " | H | 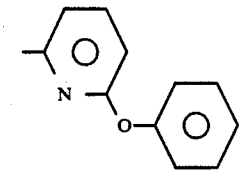 | |
| 143 | " | H | 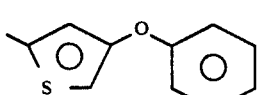 | |
| 144 | " | CN | 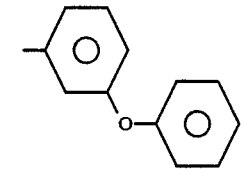 | |
| 145 | 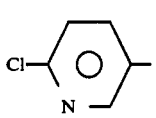 | H | 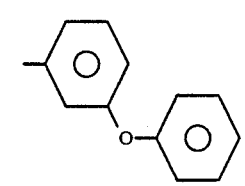 | |
| 146 | " | H | 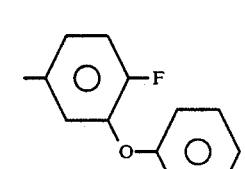 | |
| 147 | " | H | 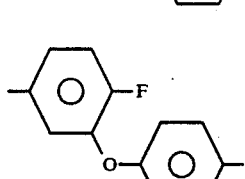 | |
| 148 | " | H | 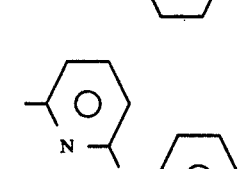 | |
| 149 | " | H | 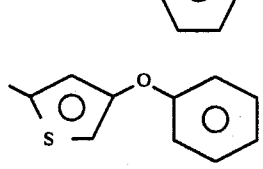 | |

TABLE 2-continued

M = C; R² = R³ = CH₃

| No. | R¹ | R⁴ | R⁵ | Physical data |
|-----|-----|-----|-----|---------------|
| 150 | " | CN | phenyl-O-phenyl | |
| 151 | [methylenedioxy-tetrahydropyridine] | H | phenyl-O-phenyl | |
| 152 | " | H | (2-F-phenyl)-O-phenyl | |
| 153 | " | H | (2-F-phenyl)-O-(4-F-phenyl) | |
| 154 | " | H | pyridyl-O-phenyl | |
| 155 | " | H | thienyl-O-phenyl | |
| 156 | " | CN | phenyl-O-phenyl | |
| 157 | $F_3C-CH_2-O$-pyridyl | H | phenyl-O-phenyl | b.p.$_{0.001}$ = 225–235° C. |

TABLE 2-continued

M = C; R² = R³ = CH₃

| No. | R¹ | R⁴ | R⁵ | Physical data |
|---|---|---|---|---|
| 158 | " | H | 4-(2-fluorophenoxy)phenyl | b.p.$_{0.01}$ = 220–230° C. |
| 159 | " | H | 4-(4-fluoro-2-fluorophenoxy)phenyl | b.p.$_{0.01}$ = 230–235° C. |
| 160 | " | H | 6-methyl-2-phenoxypyridinyl | |
| 161 | " | H | 5-methyl-3-phenoxythienyl | |
| 162 | " | CN | 3-phenoxyphenyl | |
| 163 | F—CH$_2$—CH$_2$—O—(5-methylpyridin-2-yl) | H | 3-phenoxyphenyl | |
| 164 | " | H | 4-(2-fluorophenoxy)phenyl | b.p.$_{0.001}$ = 235° C. |
| 165 | " | H | 4-(4-fluoro-2-fluorophenoxy)phenyl | |

TABLE 2-continued

| No. | R¹ | M = C; R² = R³ = CH₃ | | Physical data |
|---|---|---|---|---|
| | | R⁴ | R⁵ | |
| 166 | " | H | 6-(phenoxy)pyridin-2-yl | |
| 167 | " | H | 5-methyl-3-(phenoxy)thiophen-2-yl (approx.) | |
| 168 | " | CN | 3-(phenoxy)phenyl | |
| 169 | 2-(ethylthio)pyridin-5-yl | H | 3-(phenoxy)phenyl | |
| 170 | " | H | 2-fluoro-3-(phenoxy)phenyl | |
| 171 | " | H | 2-fluoro-3-(4-fluorophenoxy)phenyl | |
| 172 | " | H | 6-(phenoxy)pyridin-2-yl | |
| 173 | " | H | 5-methyl-3-(phenoxy)thiophen-2-yl | |
| 174 | " | CN | 3-(phenoxy)phenyl | |

TABLE 2-continued
M = C; R² = R³ = CH₃
| No. | R¹ | R⁴ | R⁵ | Physical data |
|---|---|---|---|---|
| 175 | 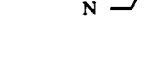 | H | 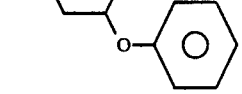 | |
| 176 | " | H | 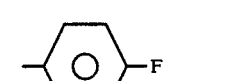 | |
| 177 | " | H |  | |
| 178 | " | H | 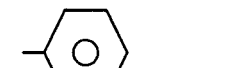 | |
| 179 | " | H | 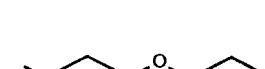 | |
| 180 | " | CN | 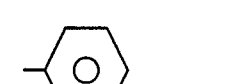 | |
| 181 | 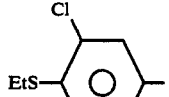 | H |  | b.p.₀.₀₀₁ = 230–240° C. |
| 182 | " | H |  | b.p.₀.₀₀₁ = 240° C. |

TABLE 2-continued
| | | M = C; R² = R³ = CH₃ | | |
|---|---|---|---|---|
| No. | R¹ | R⁴ | R⁵ | Physical data |
| 183 | " | H | 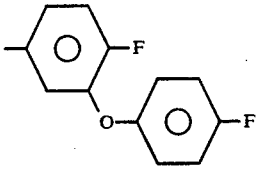 | |
| 184 | " | H | 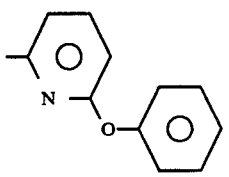 | |
| 185 | " | H | 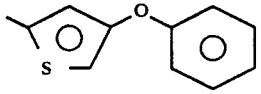 | |
| 186 | " | CN | 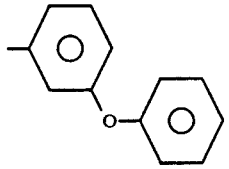 | |
| 187 | 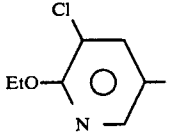 | H | 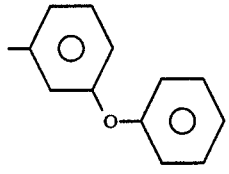 | b.p.$_{0.001}$ = 235–240° C. |
| 188 | " | H | 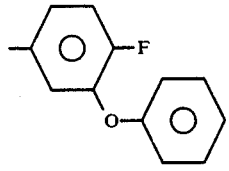 | b.p.$_{0.003}$ = 240° C. |
| 189 | " | H | 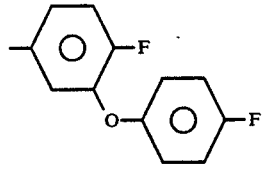 | |
| 190 | " | H | 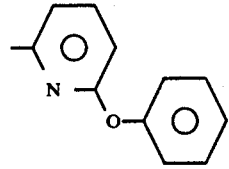 | |
| 191 | " | H | 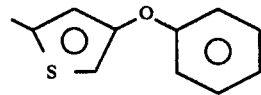 | |

TABLE 2-continued

M = C; R² = R³ = CH₃

| No. | R¹ | R⁴ | R⁵ | Physical data |
|---|---|---|---|---|
| 192 | " | CN | (phenoxyphenyl) | |
| 193 | 2,3-dichloropyridin-5-yl | H | (phenoxyphenyl) | |
| 194 | " | H | (2-fluoro-phenoxyphenyl) | |
| 195 | " | H | (2-fluoro-4'-fluoro-phenoxyphenyl) | |
| 196 | " | H | (pyridin-2-yloxyphenyl) | |
| 197 | " | H | (thien-2-yl-phenoxy) | |
| 198 | " | CN | (phenoxyphenyl) | b.p.$_{0.001}$ = 220–225° C. |
| 199 | 3-chloro-2-(2,2,2-trifluoroethoxy)pyridin-5-yl | H | (phenoxyphenyl) | |

TABLE 2-continued
M = C; R² = R³ = CH₃
| No. | R¹ | R⁴ | R⁵ | Physical data |
|-----|----|----|----|---------------|
| 200 | " | H | 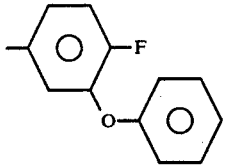 | b.p.·0.003 = 230° C. |
| 201 | " | H | 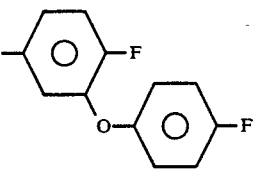 | |
| 202 | " | H | 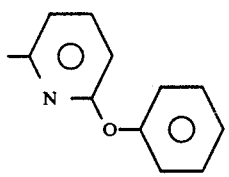 | |
| 203 | " | H | 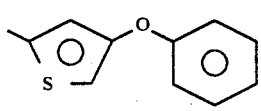 | |
| 204 | " | CN | 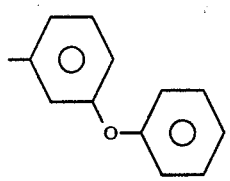 | |
| 205 | 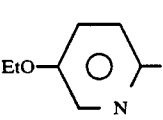 | | 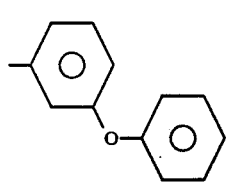 | |
| 206 | " | H | 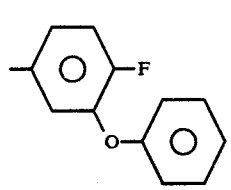 | |
| 207 | " | H | 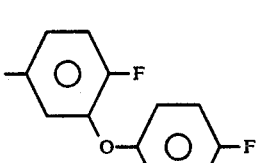 | |

TABLE 2-continued

| | | M = C; R² = R³ = CH₃ | | |
|---|---|---|---|---|
| No. | R¹ | R⁴ | R⁵ | Physical data |
| 208 | " | H | [6-methylpyridin-2-yl-oxy-phenyl] | |
| 209 | " | H | [5-methylthiophen-3-yl-oxy-phenyl] | |
| 210 | " | CN | [phenyl-oxy-phenyl] | |
| 211 | [5-chloro-2-methylpyridinyl] | H | [phenyl-oxy-phenyl] | |
| 212 | " | H | [phenyl with F, oxy-phenyl] | |
| 213 | " | H | [phenyl with F, oxy-4-fluorophenyl] | |
| 214 | " | H | [6-methylpyridin-2-yl-oxy-phenyl] | |
| 215 | " | H | [5-methylthiophen-3-yl-oxy-phenyl] | |
| 216 | " | CN | [phenyl-oxy-phenyl] | |

TABLE 2-continued $M = C; R^2 = R^3 = CH_3$

| No. | R¹ | R⁴ | R⁵ | Physical data |
|---|---|---|---|---|
| 217 | 4-methylpyridin-2-yl (H₃C-pyridine) | H | phenyl-O-phenyl | |
| 218 | " | H | (2-F-phenyl)-O-phenyl | |
| 219 | " | H | (2-F-phenyl)-O-(4-F-phenyl) | |
| 220 | " | H | (6-methylpyridin-2-yl)-O-phenyl | |
| 221 | " | H | (5-methylthien-3-yl)-O-phenyl | |
| 222 | " | CN | phenyl-O-phenyl | |
| 223 | 5-bromopyridin-2-yl (Br-pyridine) | H | phenyl-O-phenyl | |
| 224 | " | H | (2-F-phenyl)-O-phenyl | |

TABLE 2-continued
M = C; R² = R³ = CH₃
| No. | R¹ | R⁴ | R⁵ | Physical data |
|-----|----|----|----|---------------|
| 225 | " | H | 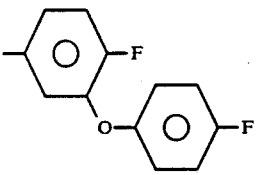 | |
| 226 | " | H | 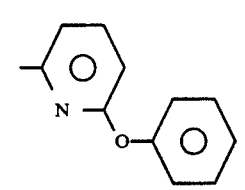 | |
| 227 | " | H | 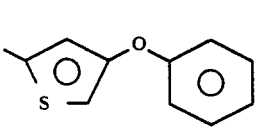 | |
| 228 | " | CN | 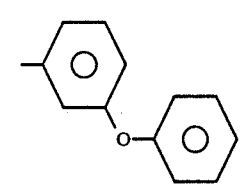 | |
| 229 | 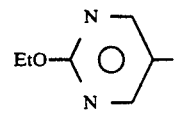 | H | 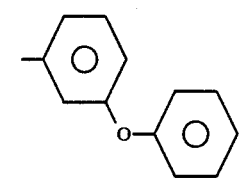 | |
| 230 | " | H | 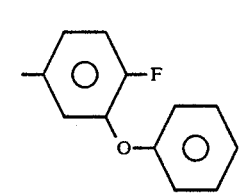 | |
| 231 | " | H | 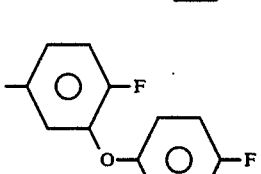 | |
| 232 | " | H | 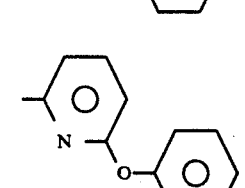 | |
| 233 | " | H | 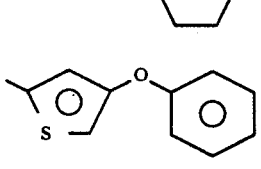 | |

TABLE 2-continued
M = C; R² = R³ = CH₃
| No. | R¹ | R⁴ | R⁵ | Physical data |
|-----|----|----|----|---------------|
| 234 | " | CN | 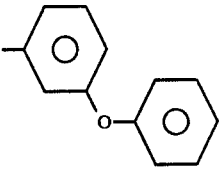 | |
| 235 | 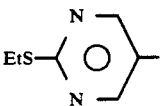 | H | 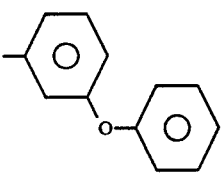 | |
| 236 | " | H | 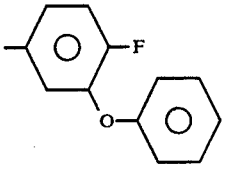 | |
| 237 | " | H | 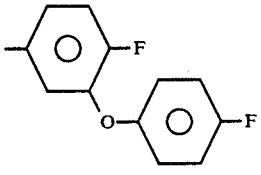 | |
| 238 | " | H | 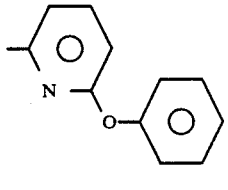 | |
| 239 | " | H | 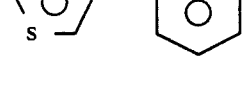 | |
| 240 | " | CN | 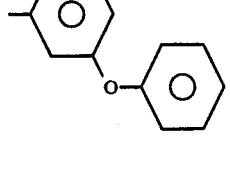 | |
| 241 | 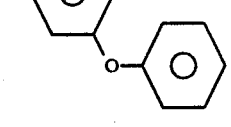 | | 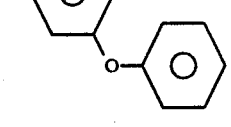 | |

TABLE 2-continued
M = C; R² = R³ = CH₃
| No. | R¹ | R⁴ | R⁵ | Physical data |
|-----|----|----|----|----|
| 242 | " | H | 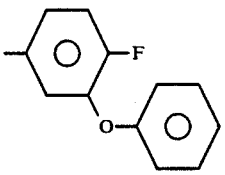 | |
| 243 | " | H | 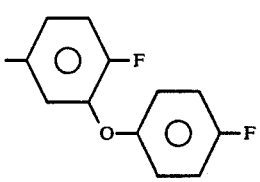 | |
| 244 | " | H | 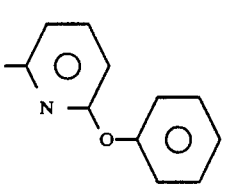 | |
| 245 | " | H | 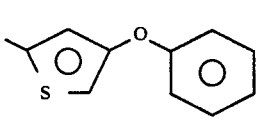 | |
| 246 | " | CN | 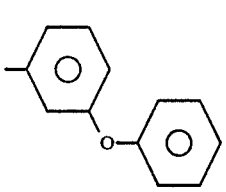 | |
| 247 | F—CH₂—CH₂—O—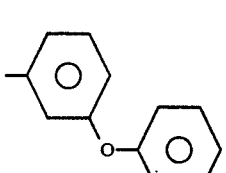 | H | 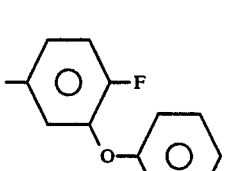 | |
| 248 | " | H | 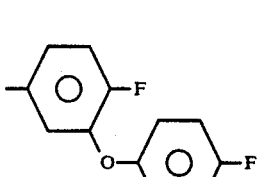 | |
| 249 | " | H | | |

TABLE 2-continued

| | | M = C; R² = R³ = CH₃ | | |
|---|---|---|---|---|
| No. | R¹ | R⁴ | R⁵ | Physical data |
| 250 | " | H | 6-methylpyridin-2-yl O-phenyl | |
| 251 | " | H | 5-methylthiophen-3-yl O-phenyl | |
| 252 | " | CN | 3-methylphenyl O-phenyl | |
| 253 | 5-ethoxy-2-methylpyrimidinyl | H | 3-methylphenyl O-phenyl | |
| 254 | " | H | 3-methyl-2-fluorophenyl O-phenyl | |
| 255 | " | H | 3-methyl-2-fluorophenyl O-(4-fluorophenyl) | |
| 256 | " | H | 6-methylpyridin-2-yl O-phenyl | |
| 257 | " | H | 5-methylthiophen-3-yl O-phenyl | |
| 258 | " | CN | 3-methylphenyl O-phenyl | |

TABLE 2-continued
| | | M = C; $R^2 = R^3 = CH_3$ | | |
|---|---|---|---|---|
| No. | $R^1$ | $R^4$ | $R^5$ | Physical data |
| 259 | 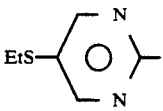 | H | 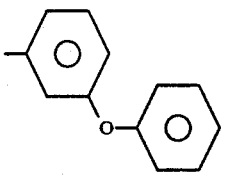 | |
| 260 | " | H | 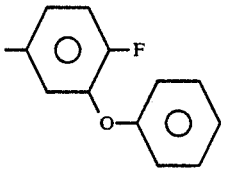 | |
| 261 | " | H | 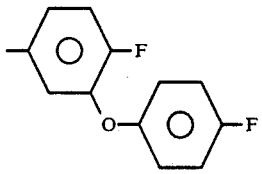 | |
| 262 | " | H | 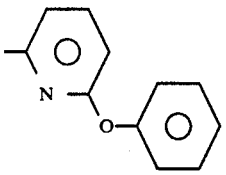 | |
| 263 | " | H | 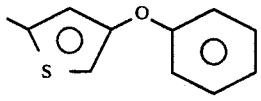 | |
| 264 | " | CN | 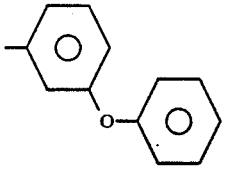 | |
| 265 | 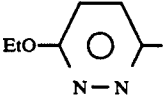 | H | 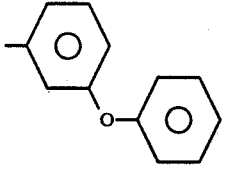 | |
| 266 | " | H | 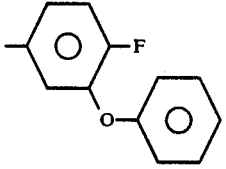 | |

TABLE 2-continued
| | | M = C; R² = R³ = CH₃ | | |
| No. | R¹ | R⁴ | R⁵ | Physical data |
| 267 | " | H | 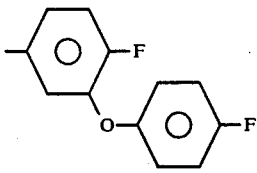 | |
| 268 | " | H | 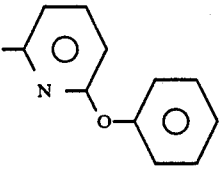 | |
| 269 | " | H | 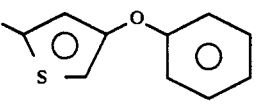 | |
| 270 | " | CN | 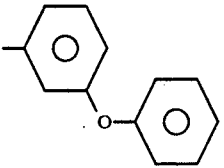 | |
| 271 | 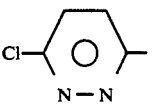 | H | 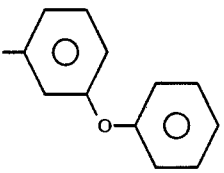 | |
| 272 | " | H | 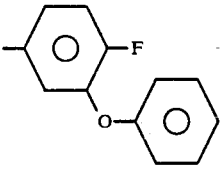 | |
| 273 | " | H | 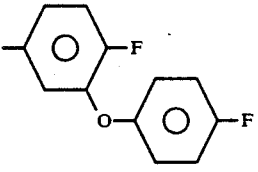 | |
| 274 | " | H | 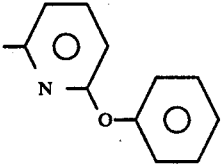 | |
| 275 | " | H | 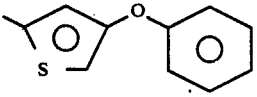 | |

TABLE 2-continued

M = C; R² = R³ = CH₃

| No. | R¹ | R⁴ | R⁵ | Physical data |
|---|---|---|---|---|
| 276 | " | CN | 4-phenoxyphenyl | |
| 277 | EtS-pyridazinyl | H | 4-phenoxyphenyl | |
| 278 | " | H | 2-fluoro-3-phenoxyphenyl | |
| 279 | " | H | 2-fluoro-3-(4-fluorophenoxy)phenyl | |
| 280 | " | H | 6-phenoxypyridin-2-yl | |
| 281 | " | H | 5-phenoxythien-2-yl | |
| 282 | " | CN | 3-phenoxyphenyl | |
| 283 | F₃C—CH₂—O-pyridazinyl | H | 3-phenoxyphenyl | |

TABLE 2-continued

M = C; R² = R³ = CH₃

| No. | R¹ | R⁴ | R⁵ | Physical data |
|-----|----|----|----|----|
| 284 | " | H | phenyl-O-phenyl with F ortho to O | |
| 285 | " | H | phenyl-O-(4-F-phenyl) with F ortho to O | |
| 286 | " | H | pyridyl-O-phenyl | |
| 287 | " | H | thienyl-O-phenyl | |
| 288 | " | CN | phenyl-O-phenyl | |
| 289 | EtO-pyrazinyl | H | phenyl-O-phenyl | |
| 290 | " | H | phenyl-O-phenyl with F ortho to O | |
| 291 | " | H | phenyl-O-(4-F-phenyl) with F ortho to O | |

TABLE 2-continued

| | | M = C; R² = R³ = CH₃ | | |
|---|---|---|---|---|
| No. | R¹ | R⁴ | R⁵ | Physical data |
| 292 | " | H | (6-phenoxy-2-methylpyridin-3-yl) | |
| 293 | " | H | (5-methyl-3-phenoxythiophen-2-yl via S) | |
| 294 | " | CN | (3-methyl-5-phenoxyphenyl) | |
| 295 | EtS-(oxazole with two N) | H | (3-methyl-5-phenoxyphenyl) | |
| 296 | " | H | (3-methyl-5-(2-fluorophenoxy)phenyl) | |
| 297 | " | H | (3-methyl-5-(2-fluoro-(4-fluorophenoxy))phenyl) | |
| 298 | " | H | (6-phenoxy-2-methylpyridin-3-yl) | |
| 299 | " | H | (5-methyl-3-phenoxythiophen-2-yl) | |
| 300 | " | CN | (3-methyl-5-phenoxyphenyl) | |

TABLE 2-continued

M = C; R² = R³ = CH₃

| No. | R¹ | R⁴ | R⁵ | Physical data |
|-----|----|----|----|---------------|
| 301 | F₃C—CH₂—O-(pyrimidine) | H | phenyl-O-phenyl | |
| 302 | " | H | phenyl(F)-O-phenyl | |
| 303 | " | H | phenyl(F)-O-phenyl(F) | |
| 304 | " | H | pyridyl-O-phenyl | |
| 305 | " | H | thienyl-O-phenyl | |
| 306 | " | CN | phenyl-O-phenyl | |
| 307 | Br-(pyrazine) | H | phenyl-O-phenyl | |
| 308 | " | H | phenyl(F)-O-phenyl | |

TABLE 2-continued
| No. | R¹ | M = C; R² = R³ = CH₃ | | Physical data |
|---|---|---|---|---|
| | | R⁴ | R⁵ | |
| 309 | " | H | 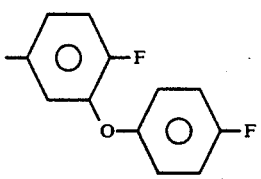 | |
| 310 | " | H | 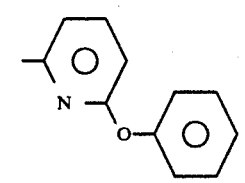 | |
| 311 | " | H | 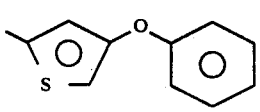 | |
| 312 | " | CN | 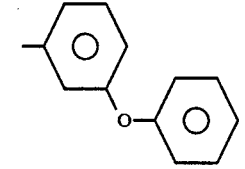 | |
| 313 | 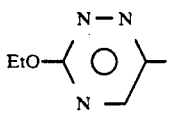 | H | 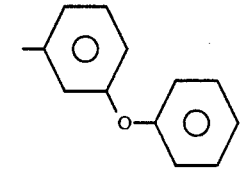 | |
| 314 | " | H | 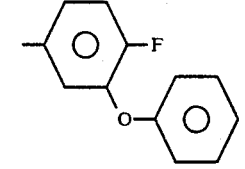 | |
| 315 | " | H | 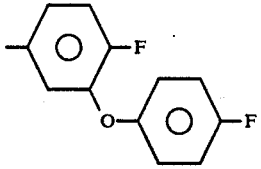 | |
| 316 | " | H | 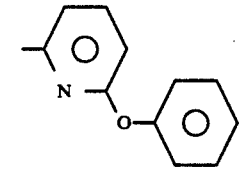 | |
| 317 | " | H | 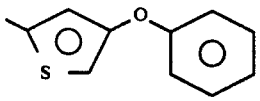 | |

TABLE 2-continued
M = C; R² = R³ = CH₃
| No. | R¹ | R⁴ | R⁵ | Physical data |
|---|---|---|---|---|
| 318 | " | CN | 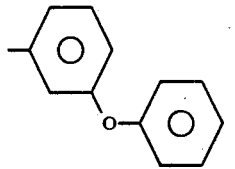 | |
| 319 | 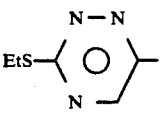 | H | 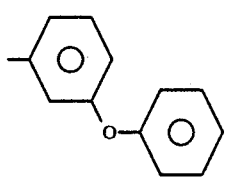 | |
| 320 | " | H | 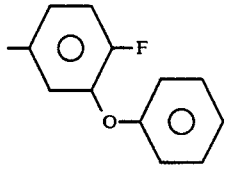 | |
| 321 | " | H | 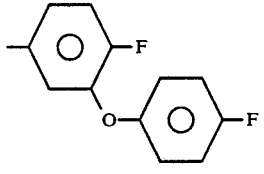 | |
| 322 | " | H | 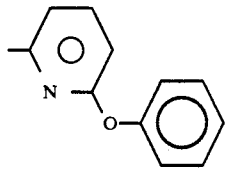 | |
| 323 | " | H | 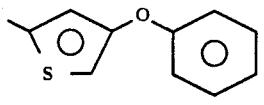 | |
| 324 | " | CN | 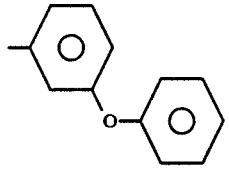 | |
| 325 | 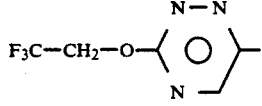 | H | 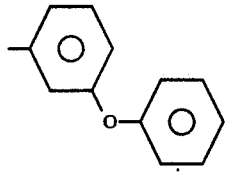 | |

TABLE 2-continued
M = C; R² = R³ = CH₃
| No. | R¹ | R⁴ | R⁵ | Physical data |
|-----|----|----|----|---------------|
| 326 | " | H | 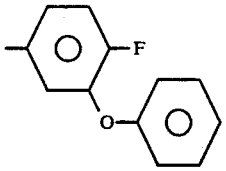 | |
| 327 | " | H | 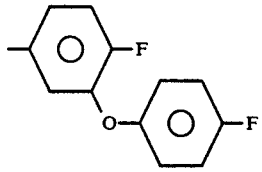 | |
| 328 | " | H | 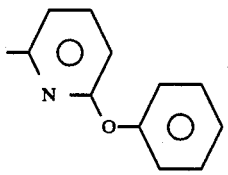 | |
| 329 | " | H | 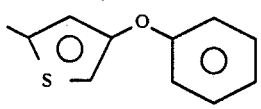 | |
| 330 | " | CN | 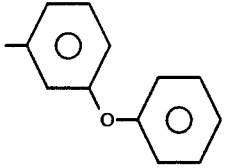 | |
| 331 | 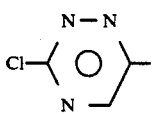 | H | 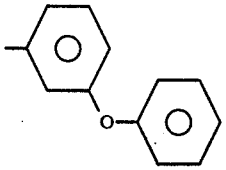 | |
| 332 | " | H | 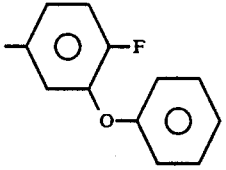 | |
| 333 | " | H | 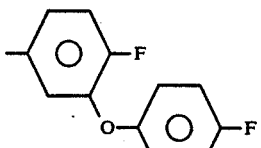 | |

TABLE 2-continued

| No. | R¹ | M = C; R² = R³ = CH₃ | | Physical data |
|-----|----|----|----|----|
| | | R⁴ | R⁵ | |
| 334 | " | H | 6-methylpyridin-2-yl phenyl ether | |
| 335 | " | H | 5-methylthiophen-3-yl phenyl ether | |
| 336 | " | CN | 3-methylphenyl phenyl ether | |
| 337 | EtO-substituted 1,2,4-triazine | H | 3-methylphenyl phenyl ether | |
| 338 | " | H | 5-methyl-2-fluorophenyl phenyl ether | |
| 339 | " | H | 5-methyl-2-fluorophenyl 4-fluorophenyl ether | |
| 340 | " | H | 6-methylpyridin-2-yl phenyl ether | |
| 341 | " | H | 5-methylthiophen-3-yl phenyl ether | |
| 342 | " | CN | 3-methylphenyl phenyl ether | |

TABLE 2-continued

M = C; R² = R³ = CH₃

| No. | R¹ | R⁴ | R⁵ | Physical data |
|---|---|---|---|---|
| 343 | EtS-[N=N, O, N ring] | H | [phenyl-O-phenyl] | |
| 344 | " | H | [phenyl-F, O-phenyl] | |
| 345 | " | H | [phenyl-F, O-phenyl-F] | |
| 346 | " | H | [pyridyl-O-phenyl] | |
| 347 | " | H | [thienyl-O-phenyl] | |
| 348 | " | CN | [phenyl-O-phenyl] | |
| 349 | F₃C—CH₂—O-[N=N, O, N ring] | H | [phenyl-O-phenyl] | |
| 350 | " | H | [phenyl-F, O-phenyl] | |

TABLE 2-continued
M = C; R² = R³ = CH₃
| No. | R¹ | R⁴ | R⁵ | Physical data |
|---|---|---|---|---|
| 351 | " | H | 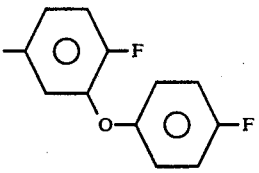 | |
| 352 | " | H | 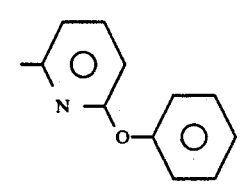 | |
| 353 | " | H | 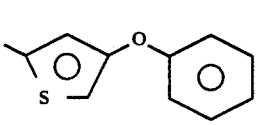 | |
| 354 | " | CN | 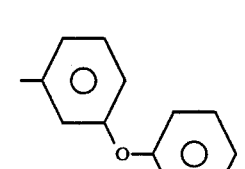 | |
| 355 | 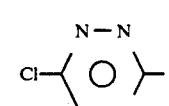 | H | 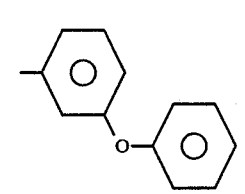 | |
| 356 | " | H | 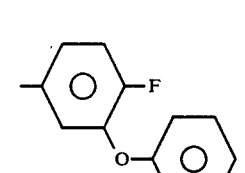 | |
| 357 | " | H | 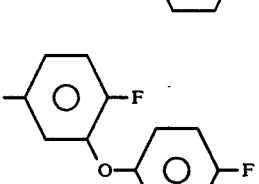 | |
| 358 | " | H | 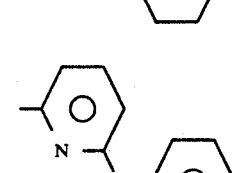 | |
| 359 | " | H | 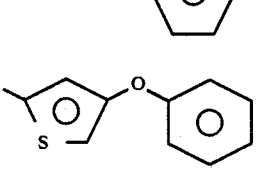 | |

TABLE 2-continued

M = C; R² = R³ = CH₃

| No. | R¹ | R⁴ | R⁵ | Physical data |
|-----|----|----|----|----|
| 360 | " | CN | 4-(phenoxy)phenyl | |
| 361 | 3-EtO-5-methyl-1,2,4,5-tetrazine | H | 4-(phenoxy)phenyl | |
| 362 | " | H | 3-fluoro-4-(phenoxy)phenyl | |
| 363 | " | H | 3-fluoro-4-(4-fluorophenoxy)phenyl | |
| 364 | " | H | 6-(phenoxy)pyridin-2-yl | |
| 365 | " | H | 4-(phenoxy)thien-2-yl | |
| 366 | " | CN | 4-(phenoxy)phenyl | |
| 367 | 3-Cl-5-methyl-1,2,4,5-tetrazine | H | 4-(phenoxy)phenyl | |

TABLE 2-continued
M = C; R² = R³ = CH₃
| No. | R¹ | R⁴ | R⁵ | Physical data |
|-----|-----|-----|-----|-----|
| 368 | " | H | 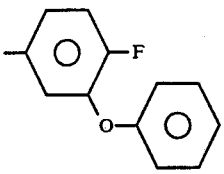 | |
| 369 | " | H | 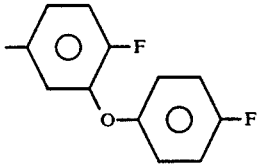 | |
| 370 | " | H | 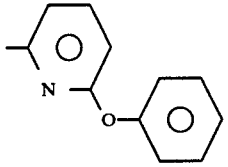 | |
| 371 | " | H | 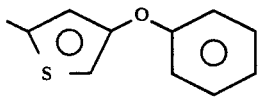 | |
| 372 | " | CN | 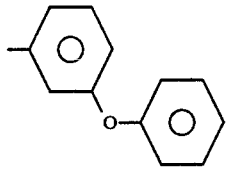 | |
| 373 | 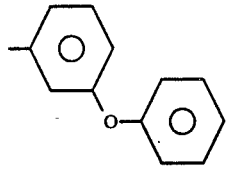 | H | 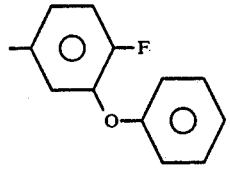 | |
| 374 | " | H | 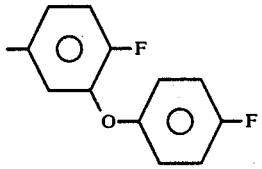 | |
| 375 | " | H | | |

TABLE 2-continued
| | | M = C; R² = R³ = CH₃ | | |
|---|---|---|---|---|
| No. | R¹ | R⁴ | R⁵ | Physical data |
| 376 | " | H | 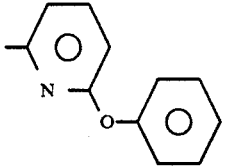 | |
| 377 | " | H | 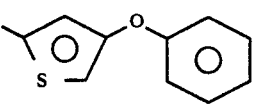 | |
| 378 | " | CN | 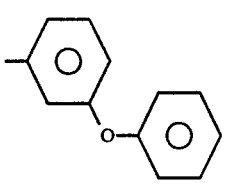 | |
| 379 | 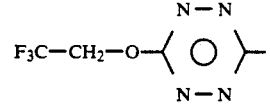 | H | 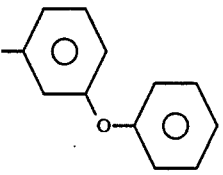 | |
| 380 | " | H | 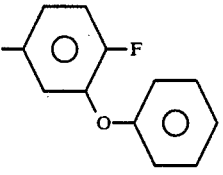 | |
| 381 | " | H | 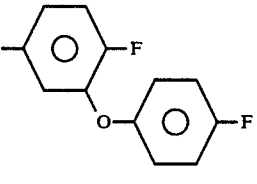 | |
| 382 | " | H | 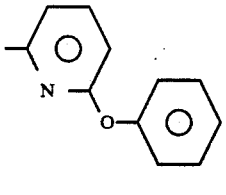 | |
| 383 | " | H | 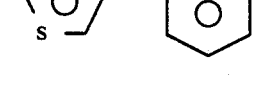 | |
| 384 | " | CN | 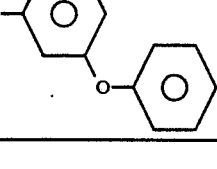 | |

TABLE 3

$M = C; R^2-R^3 = -CH_2-CH_2-$

| No. | R¹ | R⁴ | R⁵ | Physical data |
|-----|----|----|----|---------------|
| 385 | 2-EtO-pyridin-5-yl | H | 3-phenoxyphenyl | |
| 386 | " | H | 3-(2-fluorophenoxy)phenyl | |
| 387 | " | H | 3-(2-fluoro-4'-fluorophenoxy)phenyl | |
| 388 | " | H | 6-phenoxy-pyridin-3-yl | |
| 389 | " | H | 5-phenoxy-thiophen-2-yl | |
| 390 | " | CN | 3-phenoxyphenyl | |
| 391 | 2-H₃CO-pyridin-5-yl | H | 3-phenoxyphenyl | |
| 392 | " | H | 3-(2-fluorophenoxy)phenyl | |

TABLE 3-continued
M = C; R²—R³ = —CH₂—CH₂—
| No. | R¹ | R⁴ | R⁵ | Physical data |
|-----|----|----|----|---------------|
| 393 | " | H | 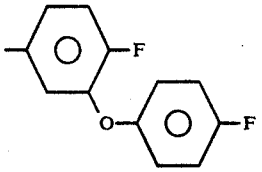 | |
| 394 | " | H | 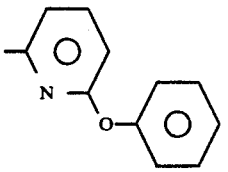 | |
| 395 | " | H | 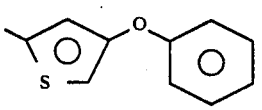 | |
| 396 | " | CN | 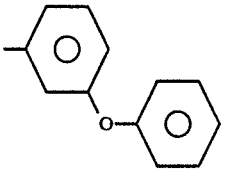 | |
| 397 | 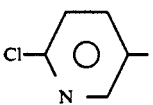 | H | 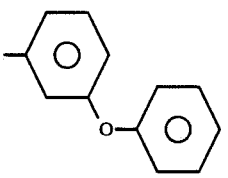 | |
| 398 | " | H | 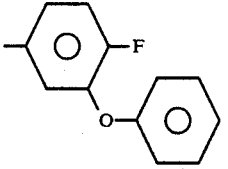 | |
| 399 | " | H | 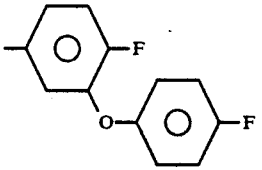 | |
| 400 | " | H | 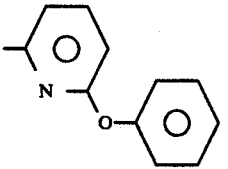 | |
| 401 | " | H | 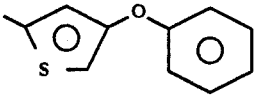 | |

TABLE 3-continued
M = C; R² —R³ = —CH₂—CH₂—
| No. | R¹ | R⁴ | R⁵ | Physical data |
|---|---|---|---|---|
| 402 | " | CN | 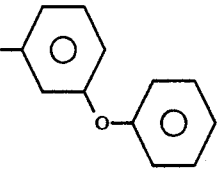 | |
| 403 | 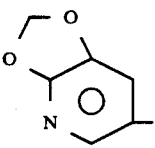 | H | 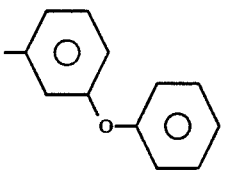 | |
| 404 | " | H | 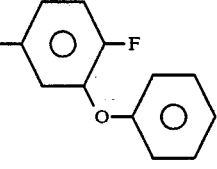 | |
| 405 | " | H | 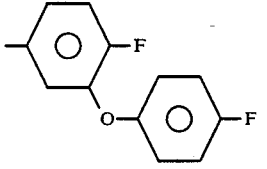 | |
| 406 | " | H | 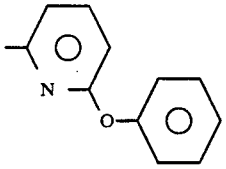 | |
| 407 | " | H | 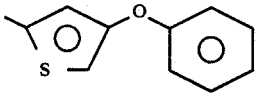 | |
| 408 | " | CN | 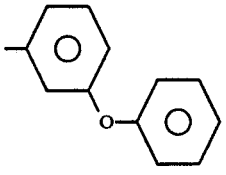 | |
| 409 | F₃C—CH₂—O— (pyridinyl) | H | 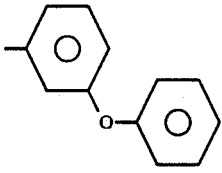 | |

TABLE 3-continued
$M = C; R^2—R^3 = —CH_2—CH_2—$
| No. | R[1] | R[4] | R[5] | Physical data |
|---|---|---|---|---|
| 410 | " | H | 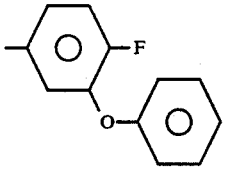 | |
| 411 | " | H | 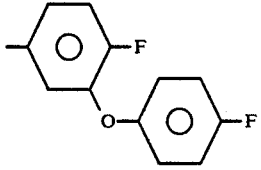 | |
| 412 | " | H | 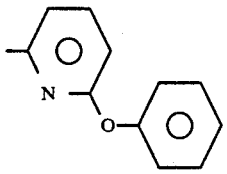 | |
| 413 | " | H | 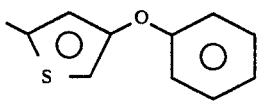 | |
| 414 | " | CN | 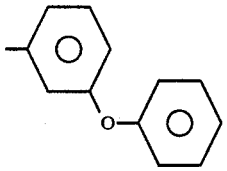 | |
| 415 | F—CH$_2$—CH$_2$—O—<structure with N pyridine> | H | 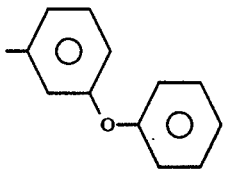 | |
| 416 | " | H | 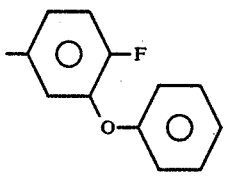 | |
| 417 | " | H | 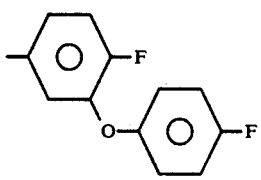 | |

TABLE 3-continued
M = C; R² —R³ = —CH₂—CH₂—
| No. | R¹ | R⁴ | R⁵ | Physical data |
|-----|----|----|----|----|
| 418 | " | H | 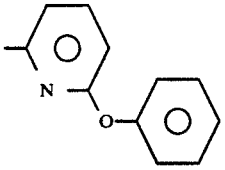 | |
| 419 | " | H | 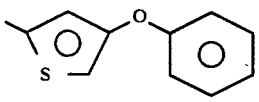 | |
| 420 | " | CN | 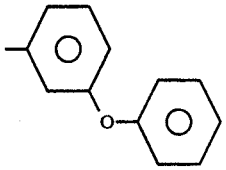 | |
| 421 | 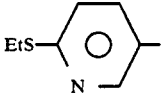 | H | 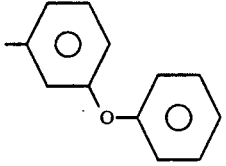 | |
| 422 | " | H | 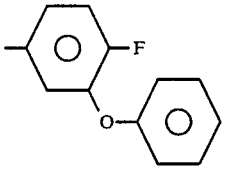 | |
| 423 | " | H | 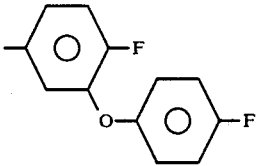 | |
| 424 | " | H | 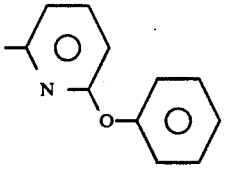 | |
| 425 | " | H | 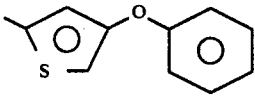 | |
| 426 | " | CN | 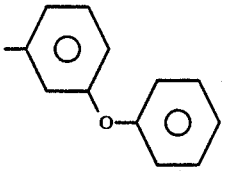 | |

TABLE 3-continued

M = C; R²—R³ = —CH₂—CH₂—

| No. | R¹ | R⁴ | R⁵ | Physical data |
|-----|----|----|----|----|
| 427 | F₃C—CH₂—S-(pyridyl) | H | phenyl-O-phenyl | |
| 428 | " | H | phenyl(F)-O-phenyl | |
| 429 | " | H | phenyl(F)-O-phenyl(F) | |
| 430 | " | H | pyridyl-O-phenyl | |
| 431 | " | H | thienyl-O-phenyl | |
| 432 | " | CN | phenyl-O-phenyl | |
| 433 | EtS-(Cl-pyridyl) | H | phenyl-O-phenyl | |
| 434 | " | H | phenyl(F)-O-phenyl | |

TABLE 3-continued
M = C; R² —R³ = —CH₂—CH₂—
| No. | R¹ | R⁴ | R⁵ | Physical data |
|---|---|---|---|---|
| 435 | " | H | 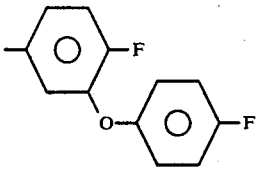 | |
| 436 | " | H | 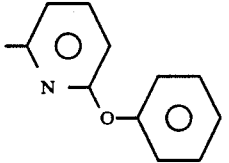 | |
| 437 | " | H | 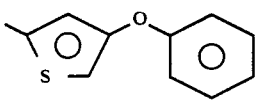 | |
| 438 | " | CN | 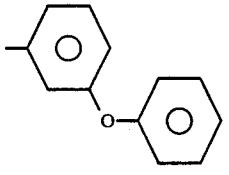 | |
| 439 | 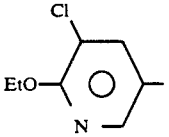 | H | 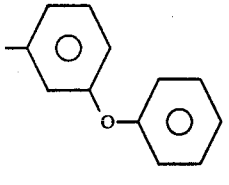 | |
| 440 | " | H | 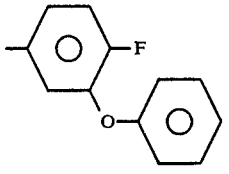 | |
| 441 | " | H | 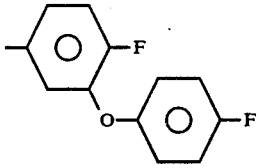 | |
| 442 | " | H | 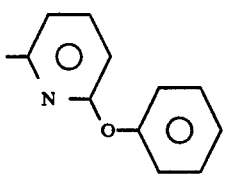 | |
| 443 | " | H | 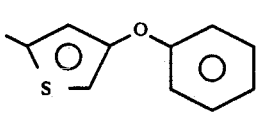 | |

TABLE 3-continued
M = C; R²—R³ = —CH₂—CH₂—
| No. | R¹ | R⁴ | R⁵ | Physical data |
|---|---|---|---|---|
| 444 | " | CN | 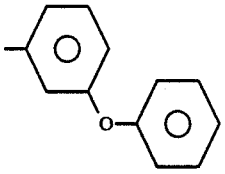 | |
| 445 | 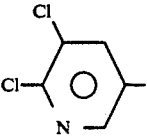 | H | 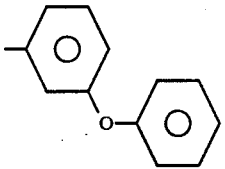 | |
| 446 | " | H | 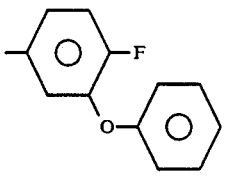 | |
| 447 | " | H | 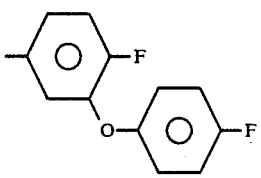 | |
| 448 | " | H | 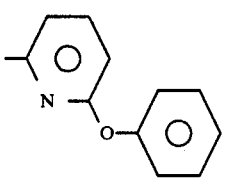 | |
| 449 | " | H | 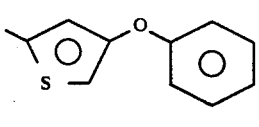 | |
| 450 | " | CN | 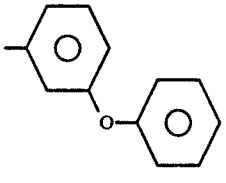 | |
| 451 | 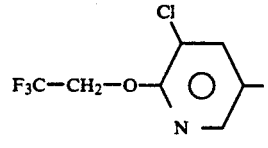 | H | 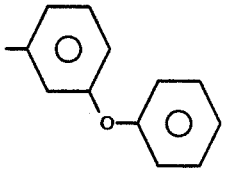 | |

TABLE 3-continued $M = C; R^2-R^3 = -CH_2-CH_2-$

| No. | R¹ | R⁴ | R⁵ | Physical data |
|---|---|---|---|---|
| 452 | " | H | 4-(2-fluoro-phenoxy)phenyl | |
| 453 | " | H | 4-(2-fluoro-4-fluorophenoxy)phenyl | |
| 454 | " | H | 6-phenoxy-pyridin-2-yl | |
| 455 | " | H | 5-phenoxy-thiophen-2-yl | |
| 456 | " | CN | 3-phenoxyphenyl | |
| 457 | 5-ethoxy-pyridin-2-yl | | 3-phenoxyphenyl | |
| 458 | " | H | 4-(2-fluoro-phenoxy)phenyl | |
| 459 | " | H | 4-(2-fluoro-4-fluorophenoxy)phenyl | |

TABLE 3-continued
M = C; R²—R³ = —CH₂—CH₂—
| No. | R¹ | R⁴ | R⁵ | Physical data |
|---|---|---|---|---|
| 460 | " | H | 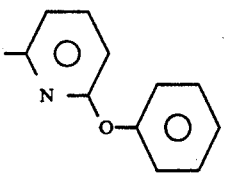 | |
| 461 | " | H | 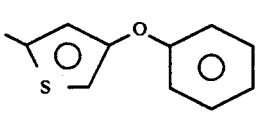 | |
| 462 | " | CN | 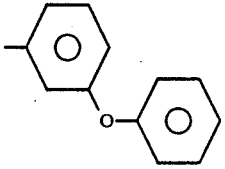 | |
| 463 | 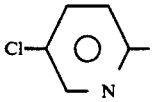 | H | 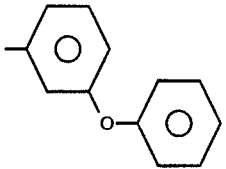 | |
| 464 | " | H | 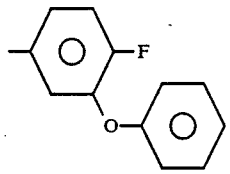 | |
| 465 | " | H | 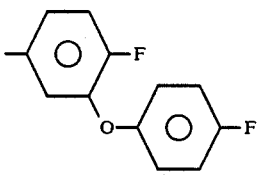 | |
| 466 | " | H | 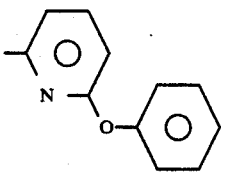 | |
| 467 | " | H | 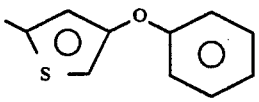 | |
| 468 | " | CN | 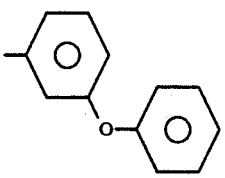 | |

TABLE 3-continued $M = C; R^2-R^3 = -CH_2-CH_2-$

| No. | R¹ | R⁴ | R⁵ | Physical data |
|---|---|---|---|---|
| 469 | 5-methylpyridin-2-yl (H₃C on pyridine, N) | H | phenyl-O-phenyl | |
| 470 | " | H | phenyl-O-(2-fluorophenyl) | |
| 471 | " | H | (2-fluorophenyl)-O-(4-fluorophenyl) | |
| 472 | " | H | pyridinyl-O-phenyl | |
| 473 | " | H | thienyl-O-phenyl | |
| 474 | " | CN | phenyl-O-phenyl | |
| 475 | 5-bromopyridin-2-yl | H | phenyl-O-phenyl | |
| 476 | " | H | (2-fluorophenyl)-O-phenyl | |

TABLE 3-continued
M = C; R²—R³ = —CH₂—CH₂—
| No. | R¹ | R⁴ | R⁵ | Physical data |
|---|---|---|---|---|
| 477 | " | H | 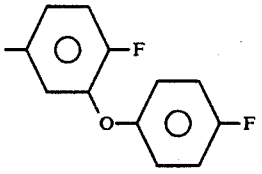 | |
| 478 | " | H | 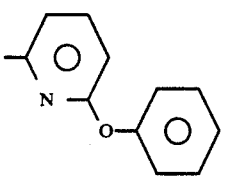 | |
| 479 | " | H | 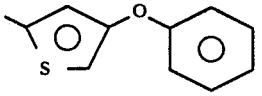 | |
| 480 | " | CN | 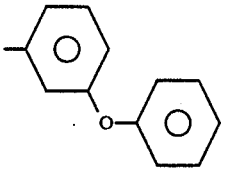 | |
| 481 | 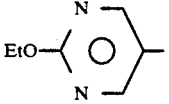 | | 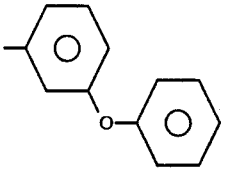 | |
| 482 | " | H | 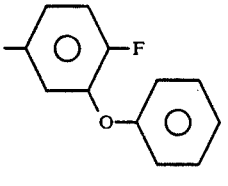 | |
| 483 | " | H | 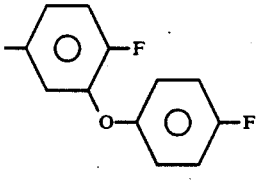 | |
| 484 | " | H | 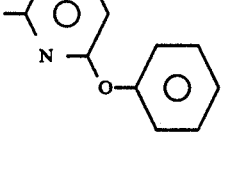 | |
| 485 | " | H |  | |

TABLE 3-continued
M = C; R² —R³ = —CH₂—CH₂—
| No. | R¹ | R⁴ | R⁵ | Physical data |
|---|---|---|---|---|
| 486 | " | CN | 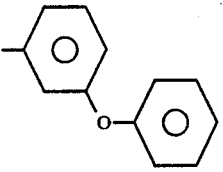 | |
| 487 | 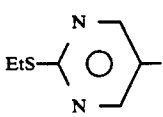 | H | 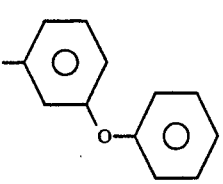 | |
| 488 | " | H | 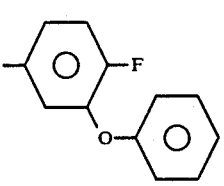 | |
| 489 | " | H | 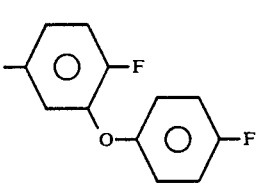 | |
| 490 | " | H | 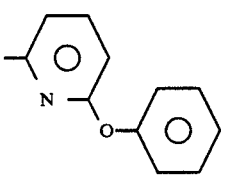 | |
| 491 | " | H | 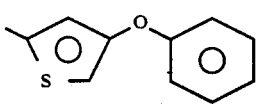 | |
| 492 | " | CN | 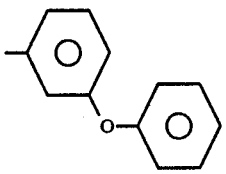 | |
| 493 | 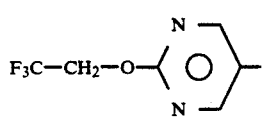 | | 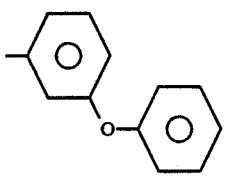 | |

TABLE 3-continued
$\underline{M = C; R^2-R^3 = -CH_2-CH_2-}$
| No. | R¹ | R⁴ | R⁵ | Physical data |
|---|---|---|---|---|
| 494 | " | H | 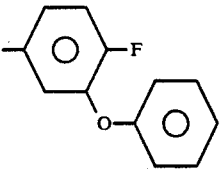 | |
| 495 | " | H | 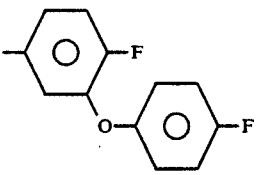 | |
| 496 | " | H | 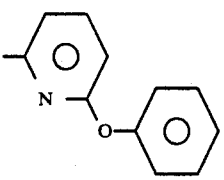 | |
| 497 | " | H | 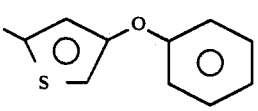 | |
| 498 | " | CN | 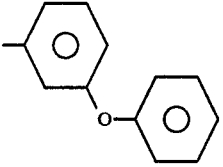 | |
| 499 | F—CH₂—CH₂—O—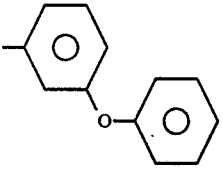— | H | 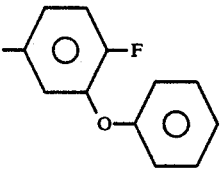 | |
| 500 | " | H | 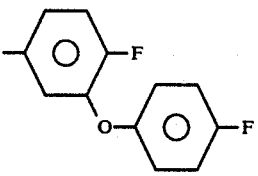 | |
| 501 | " | H | | |

TABLE 3-continued
| | M = C; $R^2$—$R^3$ = —$CH_2$—$CH_2$— | | | |
|---|---|---|---|---|
| No. | $R^1$ | $R^4$ | $R^5$ | Physical data |
| 502 | " | H | 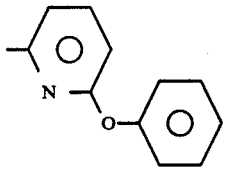 | |
| 503 | " | H | 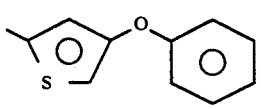 | |
| 504 | " | CN | 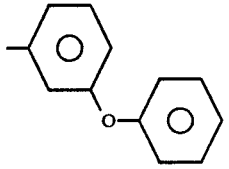 | |
| 505 | 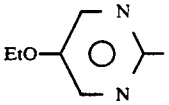 | H | 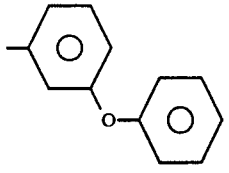 | |
| 506 | " | H | 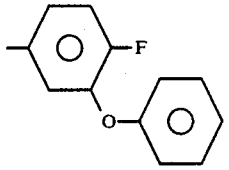 | |
| 507 | " | H | 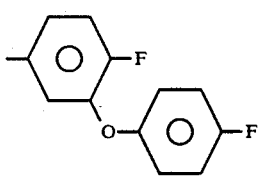 | |
| 508 | " | H | 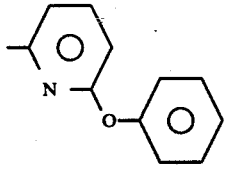 | |
| 509 | " | H | 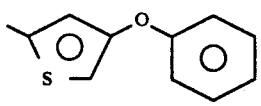 | |
| 510 | " | CN | 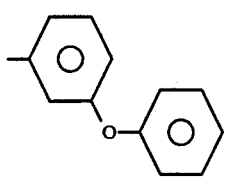 | |

TABLE 3-continued
M = C; R²—R³ = —CH₂—CH₂—
| No. | R¹ | R⁴ | R⁵ | Physical data |
|---|---|---|---|---|
| 511 | 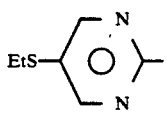 EtS—[pyrimidine] | H | 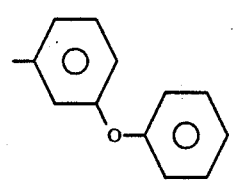 phenoxyphenyl | |
| 512 | " | H | 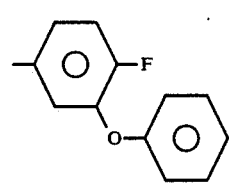 2-F-phenoxyphenyl | |
| 513 | " | H | 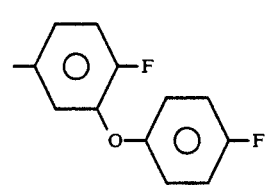 2-F,4'-F-phenoxyphenyl | |
| 514 | " | H | 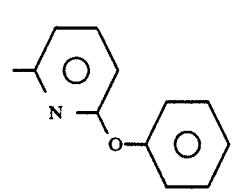 pyridinyloxyphenyl | |
| 515 | " | H | 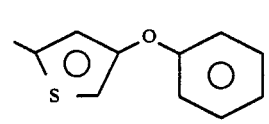 thienyloxyphenyl | |
| 516 | " | CN | 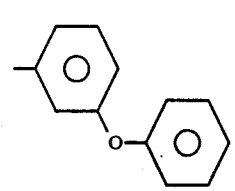 phenoxyphenyl | |
| 517 | 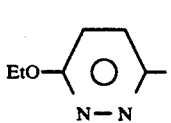 EtO—[pyridazine] | H | 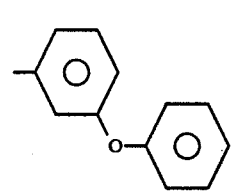 phenoxyphenyl | |
| 518 | " | H | 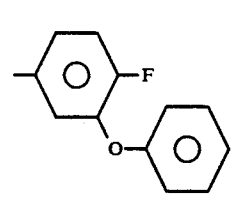 2-F-phenoxyphenyl | |

TABLE 3-continued
M = C; R²—R³ = —CH₂—CH₂—
| No. | R¹ | R⁴ | R⁵ | Physical data |
|---|---|---|---|---|
| 519 | " | H | 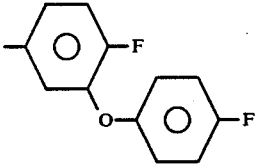 | |
| 520 | " | H | 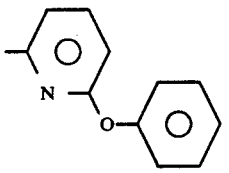 | |
| 521 | " | H | 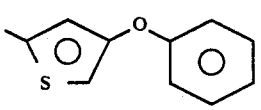 | |
| 522 | " | CN | 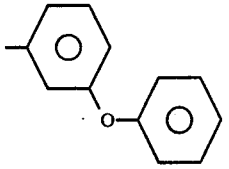 | |
| 523 | 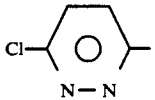 | H | 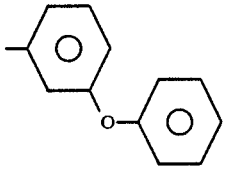 | |
| 524 | " | H | 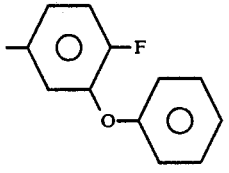 | |
| 525 | " | H | 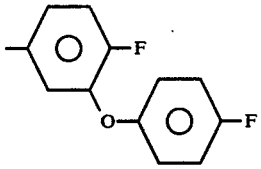 | |
| 526 | " | H | 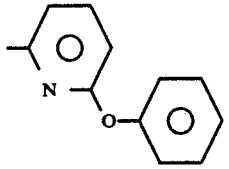 | |
| 527 | " | H | 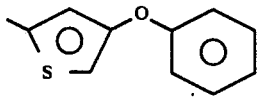 | |

TABLE 3-continued
$M = C; R^2-R^3 = -CH_2-CH_2-$
| No. | R¹ | R⁴ | R⁵ | Physical data |
|---|---|---|---|---|
| 528 | " | CN | 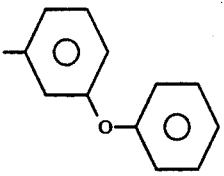 | |
| 529 | 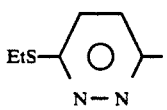 | H | 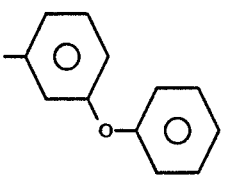 | |
| 530 | " | H | 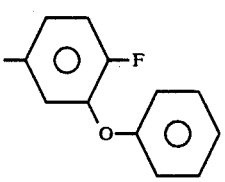 | |
| 531 | " | H | 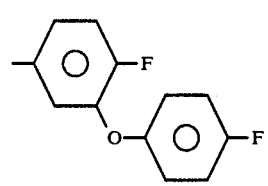 | |
| 532 | " | H | 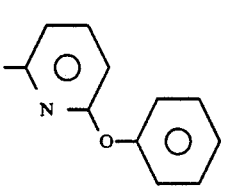 | |
| 533 | " | H | 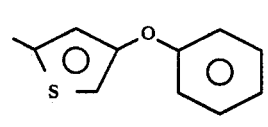 | |
| 534 | " | CN | 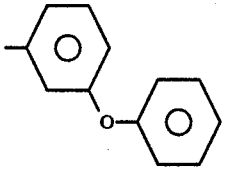 | |
| 535 | 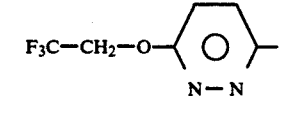 | H | 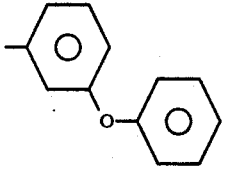 | |

TABLE 3-continued
M = C; R² —R³ = —CH₂—CH₂—
| No. | R¹ | R⁴ | R⁵ | Physical data |
|---|---|---|---|---|
| 536 | " | H | 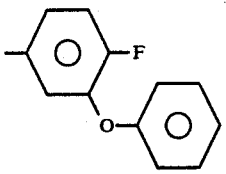 | |
| 537 | " | H | 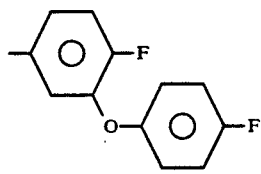 | |
| 538 | " | H | 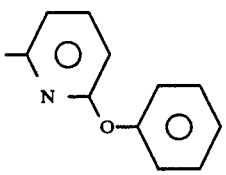 | |
| 539 | " | H | 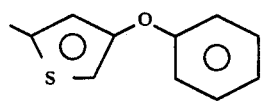 | |
| 540 | " | CN | 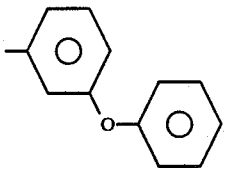 | |
| 541 | 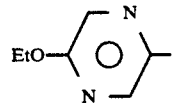 | H | 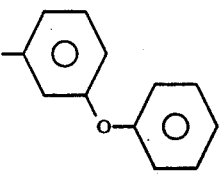 | |
| 542 | " | H | 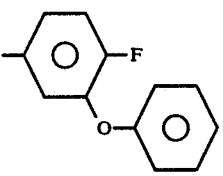 | |
| 543 | " | H | 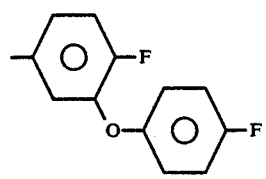 | |

TABLE 3-continued

M = C; R²—R³ = —CH₂—CH₂—

| No. | R¹ | R⁴ | R⁵ | Physical data |
|-----|----|----|----|---------------|
| 544 | " | H | 6-methyl-2-(phenoxy)pyridine | |
| 545 | " | H | 5-methyl-3-(phenoxy)thiophene | |
| 546 | " | CN | 3-methylphenyl phenyl ether | |
| 547 | 5-(ethylthio)pyrazin-2-yl | H | 3-methylphenyl phenyl ether | |
| 548 | " | H | 2-fluoro-5-methylphenyl phenyl ether | |
| 549 | " | H | 2-fluoro-5-methylphenyl 4-fluorophenyl ether | |
| 550 | " | H | 6-methyl-2-(phenoxy)pyridine | |
| 551 | " | H | 5-methyl-3-(phenoxy)thiophene | |
| 552 | " | CN | 3-methylphenyl phenyl ether | |

TABLE 3-continued
M = C; R²—R³ = —CH₂—CH₂—
| No. | R¹ | R⁴ | R⁵ | Physical data |
|---|---|---|---|---|
| 553 | 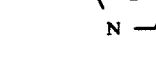 | H | 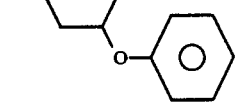 | |
| 554 | " | H | 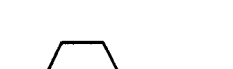 | |
| 555 | " | H | 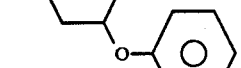 | |
| 556 | " | H | 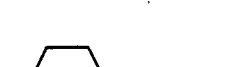 | |
| 557 | " | H | 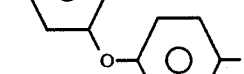 | |
| 558 | " | CN | 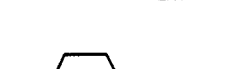 | |
| 559 |  | H | 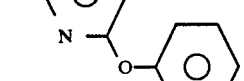 | |
| 560 | " | H | 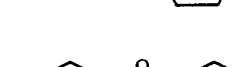 | |

TABLE 3-continued
M = C; R²—R³ = —CH₂—CH₂—
| No. | R¹ | R⁴ | R⁵ | Physical data |
|---|---|---|---|---|
| 561 | " | H | 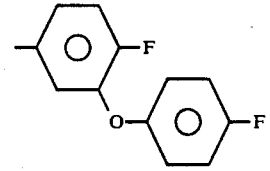 | |
| 562 | " | H | 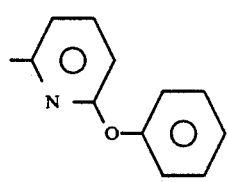 | |
| 563 | " | H | 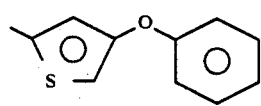 | |
| 564 | " | CN | 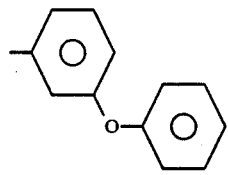 | |
| 565 | 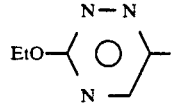 | H | 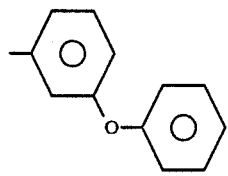 | |
| 566 | " | H | 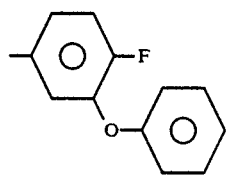 | |
| 567 | " | H | 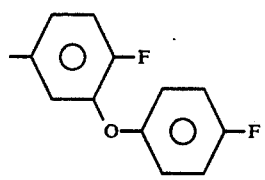 | |
| 568 | " | H | 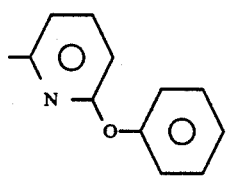 | |
| 569 | " | H | 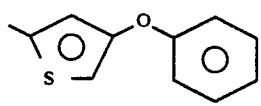 | |

TABLE 3-continued

M = C; R² —R³ = —CH₂—CH₂—

| No. | R¹ | R⁴ | R⁵ | Physical data |
|---|---|---|---|---|
| 570 | " | CN | phenoxyphenyl | |
| 571 | EtS-[1,3,4-thiadiazol-2-yl] | H | phenoxyphenyl | |
| 572 | " | H | (fluorophenoxy)phenyl | |
| 573 | " | H | (4-fluorophenoxy)(fluoro)phenyl | |
| 574 | " | H | (phenoxy)pyridinyl | |
| 575 | " | H | (phenoxy)thienyl | |
| 576 | " | CN | phenoxyphenyl | |
| 577 | F₃C—CH₂—O-[1,3,4-thiadiazol-2-yl] | H | phenoxyphenyl | |

TABLE 3-continued
M = C; R²—R³ = —CH₂—CH₂—
| No. | R¹ | R⁴ | R⁵ | Physical data |
|---|---|---|---|---|
| 578 | " | H | 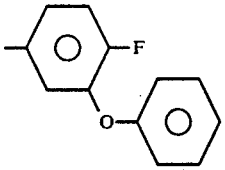 | |
| 579 | " | H | 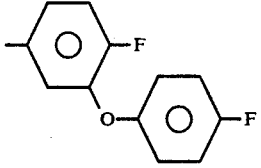 | |
| 580 | " | H | 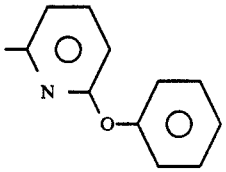 | |
| 581 | " | H | 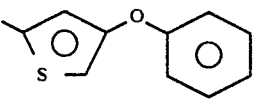 | |
| 582 | " | CN | 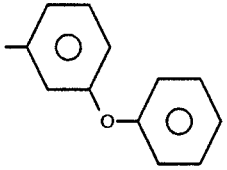 | |
| 583 | 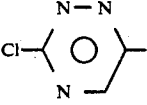 | H | 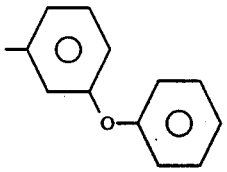 | |
| 584 | " | H | 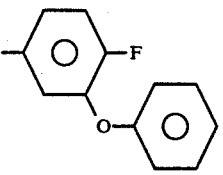 | |
| 585 | " | H | 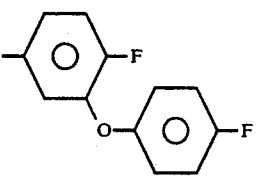 | |

TABLE 3-continued
$M = C; R^2-R^3 = -CH_2-CH_2-$
| No. | R[1] | R[4] | R[5] | Physical data |
|---|---|---|---|---|
| 586 | " | H | 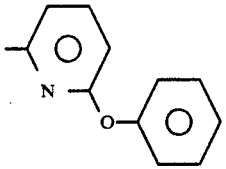 | |
| 587 | " | H | 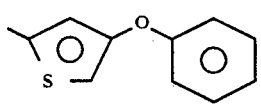 | |
| 588 | " | CN | 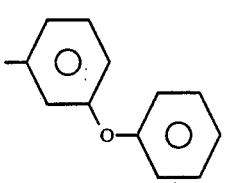 | |
| 589 | 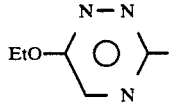 | H | 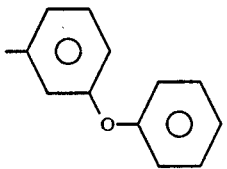 | |
| 590 | " | H | 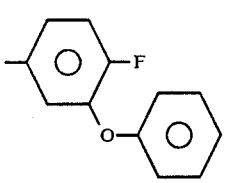 | |
| 591 | " | H | 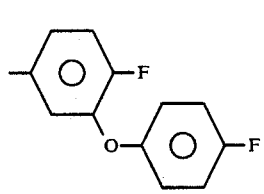 | |
| 592 | " | H | 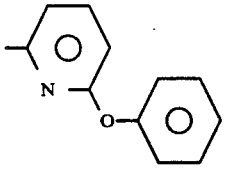 | |
| 593 | " | H | 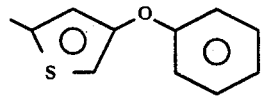 | |
| 594 | " | H | 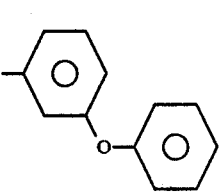 | |

TABLE 3-continued

M = C; R²—R³ = —CH₂—CH₂—

| No. | R¹ | R⁴ | R⁵ | Physical data |
|---|---|---|---|---|
| 595 | EtS-[N=N pyrimidine ring] | H | phenyl-O-phenyl | |
| 596 | " | H | phenyl(F)-O-phenyl | |
| 597 | " | H | phenyl(F)-O-phenyl(F) | |
| 598 | " | H | pyridyl-O-phenyl | |
| 599 | " | H | thienyl-O-phenyl | |
| 600 | " | CN | phenyl-O-phenyl | |
| 601 | F₃C—CH₂—O-[N=N pyrimidine ring] | H | phenyl-O-phenyl | |
| 602 | " | H | phenyl(F)-O-phenyl | |

TABLE 3-continued
M = C; R²—R³ = —CH₂—CH₂—
| No. | R¹ | R⁴ | R⁵ | Physical data |
|---|---|---|---|---|
| 603 | " | H | 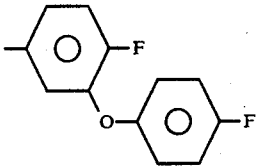 | |
| 604 | " | H | 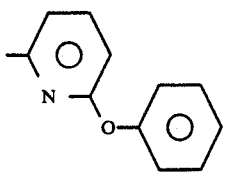 | |
| 605 | " | H | 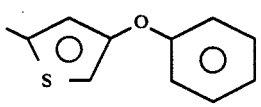 | |
| 606 | " | CN | 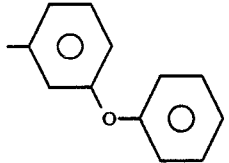 | |
| 607 | 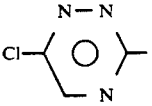 | H | 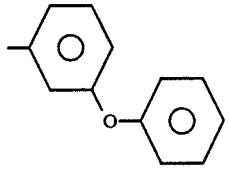 | |
| 608 | " | H | 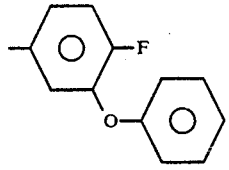 | |
| 609 | " | H | 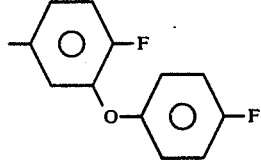 | |
| 610 | " | H | 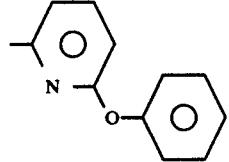 | |
| 611 | " | H | 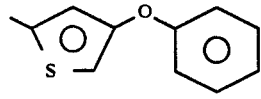 | |

TABLE 3-continued $M = C; R^2\text{—}R^3 = -CH_2-CH_2-$

| No. | R¹ | R⁴ | R⁵ | Physical data |
|---|---|---|---|---|
| 612 | " | CN | (phenyl)-O-(phenyl) | |
| 613 | EtO-[tetrazine]- | H | (phenyl)-O-(phenyl) | |
| 614 | " | H | (phenyl with F)-O-(phenyl) | |
| 615 | " | H | (phenyl with F)-O-(phenyl-F) | |
| 616 | " | H | (pyridyl)-O-(phenyl) | |
| 617 | " | H | (thienyl)-O-(phenyl) | |
| 618 | " | CN | (phenyl)-O-(phenyl) | |
| 619 | Cl-[tetrazine]- | H | (phenyl)-O-(phenyl) | |

TABLE 3-continued
M = C; R² — R³ = —CH₂—CH₂—
| No. | R¹ | R⁴ | R⁵ | Physical data |
|-----|----|----|----|---------------|
| 620 | " | H | 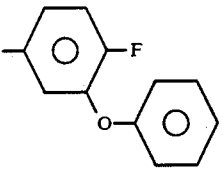 | |
| 621 | " | H | 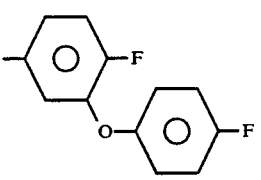 | |
| 622 | " | H | 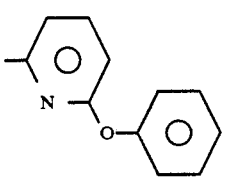 | |
| 623 | " | H | 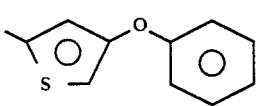 | |
| 624 | " | CN | 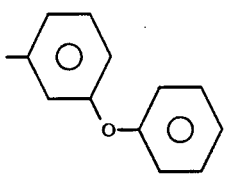 | |
| 625 | 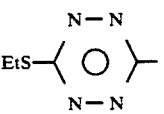 | H | 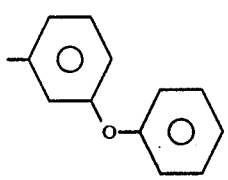 | |
| 626 | " | H | 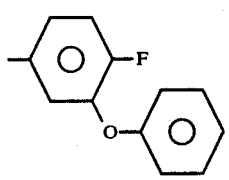 | |
| 627 | " | H | 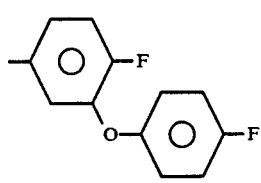 | |

TABLE 3-continued
M = C; R²—R³ = —CH₂—CH₂—
| No. | R¹ | R⁴ | R⁵ | Physical data |
|---|---|---|---|---|
| 628 | " | H | 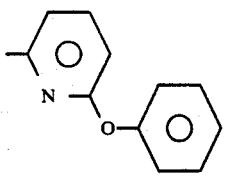 | |
| 629 | " | H | 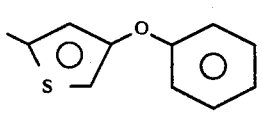 | |
| 630 | " | CN | 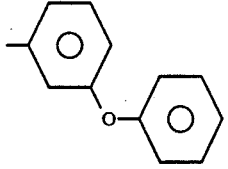 | |
| 631 | F₃C—CH₂—O—[tetrazine ring]—CH₃ | H | 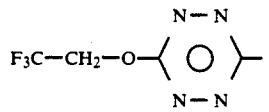 | |
| 632 | " | H | 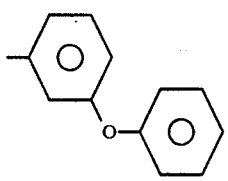 | |
| 633 | " | H | 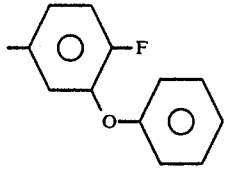 | |
| 634 | " | H | 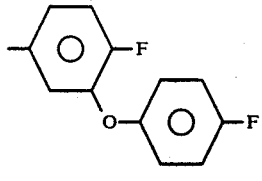 | |
| 635 | " | H | 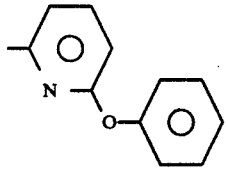 | |

TABLE 3-continued

M = C; $R^2$—$R^3$ = —$CH_2$—$CH_2$—

| No. | $R^1$ | $R^4$ | $R^5$ | Physical data |
|---|---|---|---|---|
| 636 | " | CN | 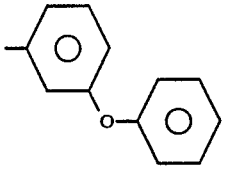 | |

BIOLOGICAL EXAMPLES

EXAMPLE 1

Bean plants (*Phaseolus v.*) which were heavily infested with greenhouse red spider mites (*Tetranychus urticae*, entire population) were sprayed with the aqueous dilution of an emulsion concentrate which contained 1,000 ppm of the respective active substance.

The mortality of the mites was checked after 7 days. 100% destruction was achieved using the compounds of Example 25, 26, 157 and 158.

EXAMPLE 2

Field beans (*Vicia faba*) showing a large number of cowpea aphid (*Aphis craccivora*) were sprayed with aqueous dilutions of wettable powder concentrates of active substance content 100 ppm until just dripping wet.

The mortality of the aphids was determined after 3 days. 100% destruction could be achieved using the compounds of Example 1, 25, 26, 133, 157 and 158.

EXAMPLE 3

The bottom insides of Petri dishes were coated with artificial nutrient medium and then sprayed with 3 ml portions of an emulsion containing 1,000 ppm of active substance after the nutrient broth had solidified. After the spray-coating had dried on, 10 cotton worm larvae (*Prodenia litura*) were placed inside and the dishes were kept for 7 days at 21° C., and the degree of activity of the respective compounds (expressed in % mortality) was then determined. In this test, the compounds 1, 2, 25, 26, 133, 134, 157 and 158 each showed an activity of 100%.

EXAMPLE 4

Bean leaves (*Phaseolus vulgaris*) were sprayed uniformly with an aqueous emulsion of the compounds at an active substance concentration of 250 ppm and placed in observation cages together with Mexican bean beetle larvae (*Epilachna varivestis*) which had been treated in the same way. After 48 hours, the compounds 1, 2, 25, 26, 133, 134, 157 and 158 showed 100% destruction of the test insects.

EXAMPLE 5

The bottom and lid insides of glass Petri dishes were lined with filter paper disks, and the latter were sprayed with 2 ml portions of an aqueous emulsion of the compounds to be tested, containing 500 ppm of active substance. 20 winged specimens of the brown plant hopper (*Nilaparvata lugens*) were subsequently inserted into each dish, the lids were put on the bottoms, and the Petri dishes were kept for 48 hours at 22° C.

After this period, the tested compounds 1, 2, 25, 26, 133, 134, 157 and 158 each showed 100% mortality of the experimental animals.

We claim:

1. A compound of formula I, its optical isomers and mixtures thereof, an agriculturally suitable salt thereof and a quaternization product thereof,

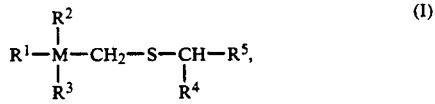

wherein:
M is Si;
$R^1$ is a radical of formula A

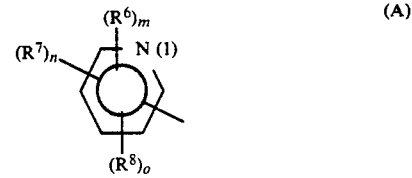

$R^2$ and $R^3$ independently of one another are ($C_1$-$C_3$)alkyl, ($C_2$-$C_8$)alkenyl, ($C_1$-$C_2$)haloalkyl, phenyl, or $R^2$ and $R^3$ taken together form an alkylene chain which, together with the quaternary central atom M, forms an unsubstituted or fluorine-substituted ring having four to six ring members;

$R^4$ is H, F, —CN, —CCl₃, —C≡CH, ($C_1$-$C_4$)alkyl or —C(=S)—NH₂;

$R^5$ is pyridyl, furyl, thienyl, all of which can be substituted by alkoxy, aryloxy or halogen, or is phthalimidyl, di($C_1$-$C_4$)alkylmaleimidyl, thiophthalimidyl, dihydrophthalimidyl, tetrahydrophthalimidyl or phenyl substituted by alkoxy, aryloxy or halogen, or $R^4$ and $R^5$, together with the carbon atom bridging them, form an indanyl or cyclopentenyl radical, which radicals can be unsubstituted or substituted by alkoxy, aryloxy or halogen;

$R^6$, $R^7$ and $R^8$ independently of one another are ($C_1$-$C_5$)alkyl, halogen, ($C_2$-$C_6$)alkenyl, ($C_2$-$C_6$)alkynyl, ($C_3$-$C_7$)cycloalkyl, ($C_1$-$C_3$)alkoxy, ($C_2$-$C_4$)alkenyloxy, ($C_2$-$C_4$)alkynyloxy, ($C_1$-$C_4$)alkylthio, ($C_3$-$C_6$)cycloalkyloxy, ($C_1$-$C_4$)haloalkyl, ($C_1$-$C_3$)haloalkoxy, ($C_1$-$C_3$)haloalkylthio, ($C_2$-$C_5$)haloalkenyl, ($C_2$-$C_5$)haloalkenyloxy, ($C_2$-$C_5$)haloalkenylthio, or two of the radicals $R^6$, $R^7$ and $R^8$, when they are in the ortho position, form a methylenedioxy, ethylenedioxy or ($C_3$-$C_5$)alkylene radical; and m, n, and o are 0, 1 or 2 provided that $0 \leq m+n+o \leq 3$.

2. A compound of formula I as claimed in claim 1, wherein $R^5$ is a radical of formula B

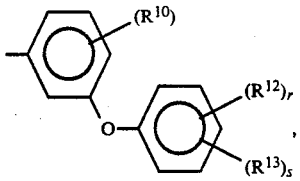

where $R^{10}$ is H or 4-fluorine,
$R^{12}$ and $R^{13}$ independently of one another are H, halogen, $(C_1-C_4)$ alkyl, $(C_1-C_4)$alkoxy or $(C_1-C_4)$haloalkyl and r and s are 0, 1 or 2 provided that $r+s$ is 0, 1 or 2; or $R^5$ is a radical of formula C

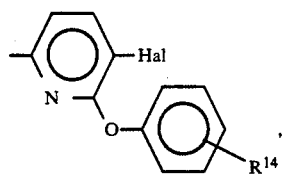

where $R^{14}$ is F, Cl, Br, $(C_1-C_4)$ alkyl, $(C_1-C_4)$alkoxy or $(C_1-C_4)$haloalkyl and Hal is F or H; or $R^5$ is a radical of formula D

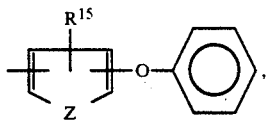

where Z is O or S and $R^{15}$ is H, halogen, $(C_1-C_4)$ alkyl, $(C_1-C_4)$alkoxy or $(C_1-C_4)$haloalkyl, CN or $NO_2$.

3. A compound of Formula I as claimed in claim 1, wherein $R^1$ is

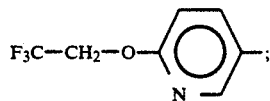

$R^2$ and $R^3$ are $CH_3$;
$R^4$ is H; and $R^5$ is

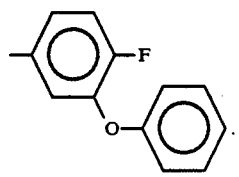

4. An insecticidal, acaricidal or nematocidal composition comprising an effective amount of a compound of formula I

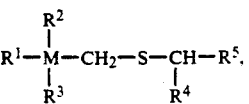

wherein:
M is Si;
$R^1$ is a radical of formula A

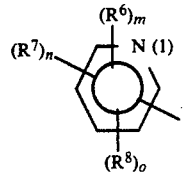

$R^2$ and $R^3$ independently of one another are $(C_1-C_3)$alkyl, $(C_2-C_8)$alkenyl, $(C_1-C_2)$haloalkyl, phenyl, or $R^2$ and $R^3$ taken together form an alkylene chain which, together with the quaternary central atom M, forms an unsubstituted or fluorine-substituted ring having four to six ring members;

$R^4$ is H, F, —CN, —$CCl_3$, —C≡CH, $(C_1-C_4)$alkyl or —C(=S)—$NH_2$;

$R^5$ is pyridyl, furyl, thienyl, all of which can be substituted by alkoxy, aryloxy or halogen, or is phthalimidyl, di$(C_1-C_4)$alkylmaleimidyl, thiophthalimidyl, dihydrophthalimidyl, tetrahydrophthalimidyl or phenyl substituted by alkoxy, aryloxy or halogen, or $R^4$ and $R^5$, together with the carbon atom bridging them, form an indanyl or cyclopentenyl radical, which radicals can be unsubstituted or substituted by alkoxy, aryloxy or halogen;

$R^6$, $R^7$ and $R^8$ independently of one another are $(C_1-C_5)$alkyl, halogen, $(C_2-C_6)$alkenyl, $(C_2-C_6)$alkynyl, $(C_3-C_7)$cycloalkyl, $(C_1-C_3)$alkoxy, $(C_2-C_4)$alkenyloxy, $(C_2-C_4)$alkynyloxy, $(C_1-C_4)$alkylthio, $(C_3-C_6)$cycloalkyloxy, $(C_1-C_4)$haloalkyl, $(C_1-C_3)$haloalkoxy, $(C_1-C_3)$haloalkylthio, $(C_2-C_5)$haloalkenyl, $(C_2-C_5)$haloalkenyloxy, $(C_2-C_5)$haloalkenylthio, or two of the radicals $R^6$, $R^7$ and $R^8$, when they are in the ortho position, form a methylenedioxy, ethylenedioxy or $(C_3-C_5)$alkylene radical; and m, n, and o are 0, 1 or 2 provided that $0 \leq m+n+o \leq 3$, and a suitable carrier therefor.

5. A method for controlling insects, acarids or nematodes which comprises applying an effective amount of a compound of formula I

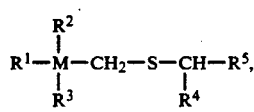

wherein:
M is Si;
$R^1$ is a radical of formula A

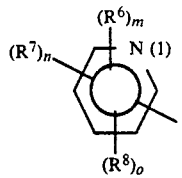
(A)

$R^2$ and $R^3$ independently of one another are $(C_1-C_3)$alkyl, $(C_2-C_8)$alkenyl, $(C_1-C_2)$haloalkyl, phenyl, or $R^2$ and $R^3$ taken together form an alkylene chain which, together with the quaternary central atom M, forms an unsubstituted or fluorine-substituted ring having four to six ring members;

$R^4$ is H, F, —CN, —CCl$_3$, —C≡CH, $(C_1-C_4)$alkyl or —C(=S)—NH$_2$;

$R^5$ is pyridyl, furyl, thienyl, all of which can be substituted by alkoxy, aryloxy or halogen, or is phthalimidyl, di$(C_1-C_4)$alkylmaleimidyl, thiophthalimidyl, dihydrophthalimidyl, tetrahydrophthalimidyl or phenyl substituted by alkoxy, aryloxy or halogen, or $R^4$ and $R^5$, together with the carbon atom bridging them, form an indanyl or cyclopentenyl radical, which radicals can be unsubstituted or substituted by alkoxy, aryloxy or halogen;

$R^6$, $R^7$ and $R^8$ independently of one another are $(C_1-C_5)$alkyl, halogen, $(C_2-C_6)$alkenyl, $(C_2-C_6)$alkynyl, $(C_3-C_7)$cycloalkyl, $(C_1-C_3)$alkoxy, $(C_2-C_4)$alkenyloxy, $(C_2-C_4)$alkynyloxy, $(C_1-C_4)$alkylthio, $(C_3-C_6)$cycloalkyloxy, $(C_1-C_4)$haloalkyl, $(C_1-C_3)$haloalkoxy, $(C_1-C_3)$haloalkylthio, $(C_2-C_5)$haloalkenyl, $(C_2-C_5)$haloalkenyloxy, $(C_2-C_5)$haloalkenylthio, or two of the radicals $R^6$, $R^7$ and $R^8$, when they are in the ortho position, form a methylenedioxy, ethylenedioxy or $(C_3-C_5)$alkylene radical; and m, n, and o are 0, 1 or 2 provided that $0 \leq m+n+o \leq 3$, to an insect, acarid or nematode or to an area, plant or substrate infested with said insect, acarid or nematode.

* * * * *